US011894127B1

(12) United States Patent
McNair

(10) Patent No.: US 11,894,127 B1
(45) Date of Patent: Feb. 6, 2024

(54) DECISION SUPPORT SYSTEMS FOR DETERMINING CONFORMITY WITH MEDICAL CARE QUALITY STANDARDS

(71) Applicant: Cerner Innovation, Inc., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 723 days.

(21) Appl. No.: 15/703,168

(22) Filed: Sep. 13, 2017

Related U.S. Application Data

(60) Provisional application No. 62/395,365, filed on Sep. 15, 2016.

(51) Int. Cl.
| | |
|---|---|
| *G16H 40/20* | (2018.01) |
| *G16H 10/60* | (2018.01) |
| *G06Q 10/0639* | (2023.01) |
| *G16H 50/70* | (2018.01) |
| *G06Q 10/067* | (2023.01) |
| *G16H 80/00* | (2018.01) |

(52) U.S. Cl.
CPC .......... *G16H 40/20* (2018.01); *G06Q 10/067* (2013.01); *G06Q 10/0639* (2013.01); *G16H 10/60* (2018.01); *G16H 50/70* (2018.01); *G16H 80/00* (2018.01)

(58) Field of Classification Search
None
See application file for complete search history.

(56) References Cited

U.S. PATENT DOCUMENTS

2015/0112700 A1* 4/2015 Sublett ............... G06Q 30/0201
    705/2
2018/0181899 A1* 6/2018 Raghavan .............. G16H 40/20

OTHER PUBLICATIONS

Neelon, Brian H et al. "A Bayesian model for repeated measures zero-inflated count data with application to outpatient psychiatric service use." Statistical modelling vol. 10,4 (2010): 421-439. doi: 10.1177/1471082X0901000404 (Year: 2010).*

* cited by examiner

*Primary Examiner* — Devin C Hein
(74) *Attorney, Agent, or Firm* — Mughal Gaudry & Franklin PC

(57) ABSTRACT

Systems, methods and computer-readable media are provided for determining conformity to performance of meaningful use measures in human health care delivery. A Bayesian Markov Chain Monte Carlo statistical process is utilized to achieve reliable estimates for such measures despite the small subgroup sample sizes accruing during each measurement period. One embodiment utilizes zero- and one-inflated beta regression that is robust against moderate prevalence of zero or one counts in the numerators for such measurements and determinations of statistical associations with such factors as clinician, care venue, and patient attributes. Based on the determined conformity, a notification is provided to provider clinicians or organization management indicating the conformity and, in some instances, a degree of conformity.

17 Claims, 17 Drawing Sheets

EXAMPLE NUMERATOR COUNTS AND PERCENTAGES (BY
CLINICIAN-CLINIC-AGE CATEGORY-GENDER)

| TOTALPATS | CLINICIAN | CLINIC | AGECAT | MIDAGE | GENDER | NAGECATGEN | FRACTION |
|---|---|---|---|---|---|---|---|
| 593 | ADKINS | | | | | | |
| | | 1 | [13-17] | 15 | FEMALE | 2 | 0.074 |
| | | 1 | [18-39] | 29 | FEMALE | 16 | 0.516 |
| | | 1 | [40-64] | 53 | FEMALE | 1 | 0.013 |
| | | 1 | [65-99] | 83 | FEMALE | 1 | 0.031 |
| | | 1 | [13-17] | 15 | MALE | 1 | 0.077 |
| | | 1 | [18-39] | 29 | MALE | 10 | 0.385 |
| | | 1 | [40-64] | 53 | MALE | 1 | 0.018 |
| | | 1 | [65-99] | 83 | MALE | 1 | 0.034 |
| | | 2 | [13-17] | 15 | FEMALE | 1 | 0.143 |
| | | 2 | [18-39] | 29 | FEMALE | 3 | 0.429 |
| | | 2 | [40-64] | 53 | FEMALE | 1 | 0.03 |
| | | 2 | [65-99] | 83 | FEMALE | 1 | 0.063 |
| | | 2 | [13-17] | 15 | MALE | 3 | 0.125 |
| | | 2 | [18-39] | 29 | MALE | 6 | 0.429 |
| | | 2 | [40-64] | 53 | MALE | 1 | 0.029 |
| | | 2 | [65-99] | 83 | MALE | 1 | 0.045 |
| | | 3 | [13-17] | 15 | FEMALE | 1 | 0.167 |
| | | 3 | [18-39] | 29 | FEMALE | 5 | 0.556 |
| | | 3 | [40-64] | 53 | FEMALE | 1 | 0.048 |
| | | 3 | [65-99] | 83 | FEMALE | 1 | 0.059 |
| | | 3 | [13-17] | 15 | MALE | 2 | 0.133 |
| | | 3 | [18-39] | 29 | MALE | 7 | 0.438 |
| | | 3 | [40-64] | 53 | MALE | 1 | 0.032 |
| | | 3 | [65-99] | 83 | MALE | 1 | 0.038 |
| 216 | ALZOLA | | | | | | |
| | | 1 | [13-17] | 15 | FEMALE | 1 | 0.063 |

FIG. 3.

EXAMPLE B: MODEL PREDICTED VS. OBSERVED ECQM CONFORMITY FRACTION

NQF 0004B

MODEL "B": Y ~ GENDER + MIDAGE, 1 CLINIC, 56 CLINICIANS

```
###############################################################

#  Bayesian zero-inflated beta model for determining relationships in AOD Meaningful
#  Use metrics measured in groups

######################################################### load JAGS Markov Chain Monte Carlo Gibbs Sampler from http://www.sourceforge.net/projects/
mcmc-jags/files
library(zoib)
library(rjags)

# load data
nqf0004b <- read.csv(file="c:/0_cerdsm/IP/eCQM_group_prevalence_ci/nqf0004b.csv",
header=TRUE,
            colClasses=c(rep("factor",3),"numeric","factor","numeric"))

#   clinician - factor with 56 levels (addiction medicine clinicians).
#   clinic - numeric factor vector with 3 levels: clinic_ids 1, 2, 3.
#   agecat - factor with 5 levels: [13-17] [18-39] [40-64] [65-99].
#   midage - numeric vector: the mid-point of each of the 4 agecat buckets rounded to the
#            nearest integer: 15 29 53 83.
#   gender - factor with 2 levels: Female Male.
#   fraction - numeric vector proportion of patients in 4 buckets of treatment counts in which they
#              had 1 or more dates with AOD treatments within 30 days of initial treatment.

######################### fit beta regression model
the Deviance Information Criterion [DIC] of a Bayesian model can be calculated using the
# function dic.samples(model) available in package rjags for model comparison purposes

####################### 3 vars by clinic executes in ~ 36 hrs on 3GHz 4-core machine - single-threaded using just one core
xb mean   |xd shape|  fixed eff x0  | fixed eff x1  | random eff z is var 1 xb
eg4 <- zoib(fraction ~ clinician*gender+midage|1|clinician*gender+midage|1, data=nqf0004b,
random=1, EUID=nqf0004b$clinic,
        zero.inflation=TRUE, one.inflation=FALSE, joint=FALSE, n.iter=4000, n.thin=20,
n.burn=1000)
362K nodes sample1 <- eg4$coeff
summary(sample1)

# check convergence of the Bayesian zero-inflated beta regression coefficients
traceplot(sample1)
autocorr.plot(sample1)
check.psrf(sample1)

# plot posterior mean of predicted y vs. observed y to check on goodness of fit
ypred <- rbind(eg4$ypred[[1]], eg4$ypred[[2]])
post.mean <- apply(ypred, 2, mean)

par(mfrow=c(1,1),mar=c(4,4,0.5,0.5))
plot(nqf0004b$fraction, post.mean, xlim=c(0,0.4), ylim=c(0,0.4), col='blue', xlab='Observed y',
ylab='Predicted y', main="")
abline(0, 1, col='red')
```

FIG. 5A

CONTINUES IN FIG. 5B

CONTINUES FROM FIG. 5A

###################### 3 vars by clinician

```
# executes in ~ 160 min on 3GHz 4-core machine - single-threaded using just one core
eg3 <- zoib(fraction ~ clinic*gender+midage|1|clinic*gender+midage|1, data=nqf0004b,
random=1, EUID=nqf0004b$clinician,
        zero.inflation=TRUE, one.inflation=FALSE, joint=FALSE, n.iter=4000, n.thin=20,
n.burn=1000)
76K nodes sample1 <- eg3$coeff
summary(sample1)
# Iterations = 1:150
# Thinning interval = 1
# Number of chains = 2
# Sample size per chain = 150

# 1. Empirical mean and standard deviation for each variable,
#    plus standard error of the mean:
#         Mean      SD    Naive SE Time-series SE
# b[1]  -1.3128489 0.070491 4.070e-03    0.0040724
# b[2]   0.3149454 0.086935 5.019e-03    0.0050216
# b[3]   0.3807631 0.091643 5.291e-03    0.0052946
# b[4]  -0.0883641 0.092735 5.354e-03    0.0058316
# b[5]  -0.0728794 0.004445 2.566e-04    0.0002567
# b[6]  -0.0706783 0.122651 7.081e-03    0.0062153
# b[7]   0.0428289 0.126848 7.324e-03    0.0080012
# b0[1] -3.5120801 0.434407 2.508e-02    0.0250314
# b0[2] -0.4906643 0.596858 3.446e-02    0.0345081
# b0[3] -1.0237072 0.654917 3.781e-02    0.0410904
# b0[4]  0.2935361 0.476600 2.752e-02    0.0261883
# b0[5]  0.0428988 0.022034 1.272e-03    0.0014363
# b0[6] -0.4923111 0.865586 4.997e-02    0.0569454
# b0[7] -0.4918497 0.882863 5.097e-02    0.0477135
# d      1.4900820 0.042577 2.458e-03    0.0022296
# sigma  0.0009419 0.001426 8.233e-05    0.0001858

# 2. Quantiles for each variable:
#          2.5%      25%       50%       75%       97.5%
# b[1]  -1.453e+00 -1.361e+00 -1.3076839 -1.265649 -1.176981*
# b[2]   1.268e-01  2.600e-01  0.3185219  0.370874  0.472689*
# b[3]   2.205e-01  3.167e-01  0.3828428  0.433084  0.573399*
# b[4]  -2.949e-01 -1.465e-01 -0.0877881 -0.023289  0.097426
# b[5]  -8.192e-02 -7.585e-02 -0.0730074 -0.069692 -0.064424*
# b[6]  -2.974e-01 -1.422e-01 -0.0742498 -0.001917  0.194773
# b[7]  -2.118e-01 -3.449e-02  0.0453895  0.131492  0.295737
# b0[1] -4.500e+00 -3.757e+00 -3.4571938 -3.202578 -2.794837*
# b0[2] -1.575e+00 -8.704e-01 -0.4899236 -0.072156  0.580748
# b0[3] -2.343e+00 -1.426e+00 -0.9807815 -0.586504  0.201140
# b0[4] -6.296e-01 -4.899e-02  0.3169751  0.612355  1.201875
# b0[5]  5.997e-04  2.750e-02  0.0427558  0.058532  0.085821*
# b0[6] -2.293e+00 -1.104e+00 -0.5277497  0.111478  1.240229
# b0[7] -2.150e+00 -1.149e+00 -0.4819491  0.127560  1.191407
# d      1.412e+00  1.463e+00  1.4886154  1.517481  1.568129*
# sigma  3.514e-07  4.638e-05  0.0003799  0.001165  0.005152*
```

*FIG. 5B*

CONTINUES IN FIG. 5C

CONTINUES FROM FIG. 5B

.
.

```
# check convergence of the Bayesian zero-inflated beta regression coefficients
traceplot(sample1)
autocorr.plot(sample1)
check.psrf(sample1)
Point est. Upper C.I.
# b[1]   1.0233930  1.1020992
# b[2]   0.9985003  1.0124892
# b[3]   0.9994186  1.0028802
# b[4]   1.0357157  1.1504409
# b[5]   0.9955321  0.9985947
# b[6]   1.0035230  1.0378990
# b[7]   1.0034037  1.0108216
# b0[1]  1.0062733  1.0531201
# b0[2]  0.9965474  1.0066510
# b0[3]  0.9958051  1.0035784
# b0[4]  0.9951282  0.9953434
# b0[5]  1.0095339  1.0677698
# b0[6]  1.0080449  1.0613780
# b0[7]  1.0048513  1.0048889
# d      0.9941768  0.9961276
# sigma  1.1378208  1.5043241
# [1] 1.166847
# $psrf.s
Point est. Upper C.I.
# b[1]   1.0233930  1.1020992
# b[2]   0.9985003  1.0124892
# b[3]   0.9994186  1.0028802
# b[4]   1.0357157  1.1504409
# b[5]   0.9955321  0.9985947
# b[6]   1.0035230  1.0378990
# b[7]   1.0034037  1.0108216
# b0[1]  1.0062733  1.0531201
# b0[2]  0.9965474  1.0066510
# b0[3]  0.9958051  1.0035784
# b0[4]  0.9951282  0.9953434
# b0[5]  1.0095339  1.0677698
# b0[6]  1.0080449  1.0613780
# b0[7]  1.0048513  1.0048889
# d      0.9941768  0.9961276
# sigma  1.1378208  1.5043241

# $psrf.m
# [1] 1.166847

# $psrf.s.summ
Point est. Upper C.I.
# Min.     0.9942    0.9953
# 1st Qu.  0.9964    1.0030
# Median   1.0030    1.0120
# Mean     1.0130    1.0630
# 3rd Qu.  1.0080    1.0630
# Max.     1.1380    1.5040
```

FIG. 5C

CONTINUES IN FIG. 5D

CONTINUES FROM FIG. 5C

```
# plot posterior mean of predicted y vs. observed y to check on goodness of fit
ypred <- rbind(eg3$ypred[[1]], eg3$ypred[[2]])
post.mean <- apply(ypred, 2, mean)

par(mfrow=c(1,1),mar=c(4,4,0.5,0.5))
plot(nqf0004b$fraction, post.mean, xlim=c(0,0.4), ylim=c(0,0.4), col='blue', xlab='Observed y',
ylab='Predicted y', main="")
abline(0, 1, col='red')

####################### 2 vars executes in ~ 90 min on 3GHz 4-core machine - single-threaded using just one core
eg2 <- zoib(fraction ~ clinic + gender|1|clinic + gender |1, data=nqf0004b, random=1,
EUID=nqf0004b$clinician,
        zero.inflation=TRUE, one.inflation=FALSE, joint=FALSE, n.iter=4000, n.thin=20,
n.burn=1000)
65K nodes sample1 <- eg2$coeff
summary(sample1)
# Iterations = 1:150
# Thinning interval = 1
# Number of chains = 2
# Sample size per chain = 150

# 1. Empirical mean and standard deviation for each variable,
#    plus standard error of the mean:

#           Mean      SD    Naive SE  Time-series SE
# b[1]   -1.67940  0.056589  0.0032672    0.0038008
# b[2]    0.24008  0.069068  0.0039877    0.0039939
# b[3]    0.34197  0.064485  0.0037230    0.0041187
# b[4]   -0.04765  0.053245  0.0030741    0.0031092
# b0[1]  -3.07113  0.274809  0.0158661    0.0145394
# b0[2]  -0.73226  0.399087  0.0230413    0.0216641
# b0[3]  -1.16762  0.446474  0.0257772    0.0258142
# b0[4]   0.05608  0.303550  0.0175255    0.0146293
# d       1.24882  0.036472  0.0021057    0.0021003
# sigma   0.00131  0.001825  0.0001054    0.0002109

# 2. Quantiles for each variable:

#          2.5%       25%        50%        75%       97.5%
# b[1]   -1.794e+00 -1.7181742 -1.6783386 -1.642440 -1.565598*
# b[2]    1.089e-01  0.1959899  0.2407940  0.289766  0.373053*
# b[3]    2.247e-01  0.2973764  0.3387673  0.383352  0.471783*
# b[4]   -1.486e-01 -0.0805934 -0.0476986 -0.011579  0.067284
# b0[1]  -3.624e+00 -3.2531487 -3.0845198 -2.891312 -2.529584*
# b0[2]  -1.525e+00 -1.0296093 -0.7093727 -0.477668  0.057478
# b0[3]  -1.977e+00 -1.4832287 -1.1555495 -0.861787 -0.384979*
# b0[4]  -5.441e-01 -0.1380782  0.0562037  0.243815  0.644924
# d       1.180e+00  1.2228315  1.2467545  1.272723  1.326504*
# sigma   4.748e-06  0.0001842  0.0007045  0.001716  0.006004*
```

*FIG. 5D*

CONTINUES IN FIG. 5E

CONTINUES FROM FIG. 5D

```
# check convergence of the Bayesian zero-inflated beta regression coefficients
traceplot(sample1)
autocorr.plot(sample1)
check.psrf(sample1)
Point est. Upper C.I.
# b[1]  1.0101459  1.0414095
# b[2]  0.9986784  1.0149791
# b[3]  1.0079411  1.0610560
# b[4]  0.9968953  1.0097741
# b0[1] 0.9960456  0.9962093
# b0[2] 1.0111089  1.0707595
# b0[3] 1.0050234  1.0237932
# b0[4] 0.9981316  1.0027990
# d     1.0153818  1.0935144
# sigma 1.0383371  1.1685781
# [1] 1.082187
# $psrf.s
Point est. Upper C.I.
# b[1]  1.0101459  1.0414095
# b[2]  0.9986784  1.0149791
# b[3]  1.0079411  1.0610560
# b[4]  0.9968953  1.0097741
# b0[1] 0.9960456  0.9962093
# b0[2] 1.0111089  1.0707595
# b0[3] 1.0050234  1.0237932
# b0[4] 0.9981316  1.0027990
# d     1.0153818  1.0935144
# sigma 1.0383371  1.1685781

# $psrf.m
# [1] 1.082187

# $psrf.s.summ
Point est. Upper C.I.
# Min.    0.9960    0.9962
# 1st Qu. 0.9983    1.0110
# Median  1.0060    1.0330
# Mean    1.0080    1.0480
# 3rd Qu. 1.0110    1.0680
Max.    1.0380    1.1690 plot posterior mean of predicted y vs. observed y to check on goodness of fit
ypred <- rbind(eg2$ypred[[1]], eg2$ypred[[2]])
post.mean <- apply(ypred, 2, mean)

par(mfrow=c(1,1),mar=c(4,4,0.5,0.5))
plot(nqf0004b$fraction, post.mean, xlim=c(0,0.4), ylim=c(0,0.4), col='blue', xlab='Observed y',
ylab='Predicted y', main="")
abline(0, 1, col='red')

######################## 1 var executes in ~ 40 min on 3GHz 4-core machine - single-threaded using just one core
eg1 <- zoib(fraction ~ clinic|1|clinic |1, data=nqf0004b, random=1, EUID=nqf0004b$clinician,
        zero.inflation=TRUE, one.inflation=FALSE, joint=FALSE, n.iter=4000, n.thin=20,
n.burn=1000)
# 50K nodes
```

FIG. 5E

CONTINUES IN FIG. 5F

CONTINUES FROM FIG. 5E

.
.

```
sample1 <- eg1$coeff
summary(sample1)
# Iterations = 1:150
# Thinning interval = 1
# Number of chains = 2
# Sample size per chain = 150

# 1. Empirical mean and standard deviation for each variable,
#    plus standard error of the mean:

#          Mean      SD    Naive SE   Time-series SE
# b[1]  -1.702765 0.054744 3.161e-03    0.0021524
# b[2]   0.247223 0.070674 4.080e-03    0.0027018
# b[3]   0.343901 0.069736 4.026e-03    0.0037721
# b0[1] -3.023967 0.225820 1.304e-02    0.0150089
# b0[2] -0.693956 0.399898 2.309e-02    0.0231108
# b0[3] -1.157508 0.441259 2.548e-02    0.0265743
# d      1.245801 0.038071 2.198e-03    0.0022011
# sigma  0.001248 0.001279 7.383e-05    0.0001791

# 2. Quantiles for each variable:

#          2.5%       25%        50%        75%       97.5%
# b[1]  -1.801e+00 -1.740332 -1.7043876 -1.664864 -1.595653*
# b[2]   1.190e-01  0.196898  0.2470008  0.296525  0.393359*
# b[3]   2.019e-01  0.296087  0.3435363  0.392022  0.476243*
# b0[1] -3.558e+00 -3.160339 -3.0240371 -2.882987 -2.613862*
# b0[2] -1.528e+00 -0.936976 -0.6671113 -0.451377 -0.002583*
# b0[3] -1.986e+00 -1.476854 -1.1162433 -0.865620 -0.275600*
# d      1.175e+00  1.220002  1.2439235  1.275142  1.317702*
sigma  2.665e-05  0.000338  0.0008005  0.001615  0.004564* check convergence of the Bayesian zero-inflated beta regression coefficients
traceplot(sample1)
autocorr.plot(sample1)
check.psrf(sample1)
Point est. Upper C.I.
# b[1]  0.9968131  0.9968172
# b[2]  0.9995752  1.0010857
# b[3]  0.9943232  0.9944604
# b0[1] 1.0395977  1.0395995
# b0[2] 1.0067048  1.0153844
# b0[3] 1.0148069  1.0571339
# d     1.0134566  1.0314500
# sigma 1.0185480  1.0444082
# [1] 1.018331
# $psrf.s
Point est. Upper C.I.
# b[1]  0.9968131  0.9968172
# b[2]  0.9995752  1.0010857
# b[3]  0.9943232  0.9944604
# b0[1] 1.0395977  1.0395995
# b0[2] 1.0067048  1.0153844
# b0[3] 1.0148069  1.0571339
# d     1.0134566  1.0314500
# sigma 1.0185480  1.0444082

```

CONTINUES IN FIG. 5G

CONTINUES FROM FIG. 5F

```
# $psrf.m
# [1] 1.018331

# $psrf.s.summ
Point est. Upper C.I.
# Min.    0.9943    0.9945
# 1st Qu. 0.9989    1.0000
# Median  1.0100    1.0230
# Mean    1.0100    1.0230
# 3rd Qu. 1.0160    1.0410
Max.    1.0400    1.0570 plot posterior mean of predicted y vs. observed y to check on goodness of fit
ypred <- rbind(eg1$ypred[[1]], eg1$ypred[[2]])
post.mean <- apply(ypred, 2, mean)

par(mfrow=c(1,1),mar=c(4,4,0.5,0.5))
plot(nqf0004b$fraction, post.mean, xlim=c(0,0.4), ylim=c(0,0.4), col='blue', xlab='Observed y',
ylab='Predicted y', main="")
abline(0, 1, col='red')

######################## 1 var executes in ~ 16 hr on 3GHz 4-core machine - single-threaded using just one core
eg0 <- zoib(fraction ~ clinician|1|clinician|1, data=nqf0004b, random=1,
EUID=nqf0004b$clinic,
        zero.inflation=TRUE, one.inflation=FALSE, joint=FALSE, n.iter=4000, n.thin=20,
n.burn=1000)
199K nodes sample1 <- eg0$coeff
summary(sample1)
file check convergence of the Bayesian zero-inflated beta regression coefficients
traceplot(sample1)
autocorr.plot(sample1)
check.psrf(sample1)
Error in chol.default(W): The leading minor of order 51 is not positive definite plot posterior mean of predicted y vs. observed y to check on goodness of fit
ypred <- rbind(eg0$ypred[[1]], eg0$ypred[[2]])
post.mean <- apply(ypred, 2, mean)

par(mfrow=c(1,1),mar=c(4,4,0.5,0.5))
plot(nqf0004b$fraction, post.mean, xlim=c(0,0.4), ylim=c(0,0.4), col='blue', xlab='Observed y',
ylab='Predicted y', main="")
abline(0, 1, col='red')

######################## 1 var
```

FIG. 5G

CONTINUES IN FIG. 5H

CONTINUES FROM FIG. 5G

```
# select by clinic and analyze separately (e.g., clinic 2)
nqf0004b_2 <- nqf0004b[nqf0004b$clinic == 2, ]

# executes in ~ 110 min on 3GHz 4-core machine - single-threaded using just one core
eg0_2 <- zoib(fraction ~ clinician|1|clinician|1, data=nqf0004b_2, random=1,
EUID=nqf0004b_2$clinic,
        zero.inflation=TRUE, one.inflation=FALSE, joint=FALSE, n.iter=4000, n.thin=20,
n.burn=1000)
68K nodes sample1 <- eg0_2$coeff
summary(sample1)
file check convergence of the Bayesian zero-inflated beta regression coefficients
traceplot(sample1)
autocorr.plot(sample1)
check.psrf(sample1)
Error in chol.default(W): The leading minor of order 50 is not positive definite plot posterior mean of predicted y vs. observed y to check on goodness of fit
ypred <- rbind(eg0_2$ypred[[1]], eg0_2$ypred[[2]])
post.mean <- apply(ypred, 2, mean)

par(mfrow=c(1,1),mar=c(4,4,0.5,0.5))
plot(nqf0004b_2$fraction, post.mean, xlim=c(0,0.4), ylim=c(0,0.4), col='blue', xlab='Observed
y', ylab='Predicted y', main="")
abline(0, 1, col='red')

##################### 1 var executes in ~ 12 min on 3GHz 4-core machine - single-threaded using just one core
eg0_2a <- zoib(fraction ~ gender+midage|1|gender+midage|1, data=nqf0004b_2, random=1,
EUID=nqf0004b_2$clinician,
        zero.inflation=TRUE, one.inflation=FALSE, joint=FALSE, n.iter=4000, n.thin=20,
n.burn=1000)
22K nodes sample1 <- eg0_2a$coeff
summary(sample1)
# Iterations = 1:150
# Thinning interval = 1
# Number of chains = 2
# Sample size per chain = 150

# 1. Empirical mean and standard deviation for each variable,
#    plus standard error of the mean:

#         Mean      SD     Naive SE  Time-series SE
# b[1]  -1.039629 0.076121 0.0043948    0.0044011
# b[2]  -0.151510 0.084175 0.0048599    0.0048614
# b[3]  -0.072646 0.007717 0.0004455    0.0004708
# b0[1] -3.984329 0.542192 0.0313035    0.0313443
# b0[2] -0.212641 0.623142 0.0359771    0.0382779
# b0[3]  0.040921 0.042083 0.0024297    0.0024311
# d      1.553310 0.071299 0.0041165    0.0041156
# sigma  0.002363 0.003606 0.0002082    0.0005410

```

*FIG. 5H*

CONTINUES IN FIG. 5I

CONTINUES FROM FIG. 5H

```
# 2. Quantiles for each variable:

#          2.5%         25%         50%         75%        97.5%
# b[1]  -1.189e+00 -1.0930092 -1.0445020 -0.988808 -0.8859423*
# b[2]  -3.365e-01 -0.2023294 -0.1506595 -0.090928  0.0006182*
# b[3]  -8.747e-02 -0.0778922 -0.0726786 -0.066636 -0.0582287*
# b0[1] -5.245e+00 -4.3100470 -3.9431761 -3.624812 -3.0890527*
# b0[2] -1.378e+00 -0.6205911 -0.2091335  0.208893  1.0126788
# b0[3] -3.954e-02  0.0172610  0.0404767  0.068350  0.1259538
# d      1.397e+00  1.5074259  1.5551686  1.596558  1.6685726*
sigma  2.077e-06  0.0001826  0.0008665  0.002722  0.0118331* check convergence of the Bayesian zero-inflated beta regression coefficients
traceplot(sample1)
autocorr.plot(sample1)
check.psrf(sample1)
Point est. Upper C.I.
# b[1]    1.0032627  1.0218231
# b[2]    1.0591761  1.2360934
# b[3]    1.0043445  1.0450967
# b0[1]   0.9952872  1.0023625
# b0[2]   0.9957879  1.0003156
# b0[3]   0.9940815  0.9954028
# d       1.0019821  1.0199502
# sigma   1.0445685  1.1753104
# [1] 1.081202
# $psrf.s
Point est. Upper C.I.
# b[1]    1.0032627  1.0218231
# b[2]    1.0591761  1.2360934
# b[3]    1.0043445  1.0450967
# b0[1]   0.9952872  1.0023625
# b0[2]   0.9957879  1.0003156
# b0[3]   0.9940815  0.9954028
# d       1.0019821  1.0199502
# sigma   1.0445685  1.1753104

# $psrf.m
# [1] 1.081202

# $psrf.s.summ
Point est. Upper C.I.
# Min.     0.9941     0.9954
# 1st Qu.  0.9957     1.0020
# Median   1.0030     1.0210
# Mean     1.0120     1.0620
# 3rd Qu.  1.0140     1.0780
# Max.     1.0590     1.2360
```

*FIG. 5I*

CONTINUES IN FIG. 5J

CONTINUES FROM FIG. 5I

.
.
.

```
# plot posterior mean of predicted y vs. observed y to check on goodness of fit
ypred <- rbind(eg0_2a$ypred[[1]], eg0_2a$ypred[[2]])
post.mean <- apply(ypred, 2, mean)

par(mfrow=c(1,1),mar=c(4,4,0.5,0.5))
plot(nqf0004b_2$fraction, post.mean, xlim=c(0,0.4), ylim=c(0,0.4), col='blue', xlab='Observed y', ylab='Predicted y', main="")
abline(0, 1, col='red')

# ****************************************************************************
# * List of parameter for which the posterior samples are generated           *
# * b: regression coeff in the linear predictor for the mean of beta distrib  *
# * b0: regression coeff in the linear predictor for Prob(y=0)                *
# * b1: regression coeff in the linear predictor for Prob(y=1)                *
# * d: regression coeff in the linear predictor for the sum of the two shape  *
# *    parameters in the beta distrib                                         *
# * sigma: standard deviation of each random variable                         *
**************************************************************************** extract model coefficient values from JAGS Bayesian MCMC beta regression model object
for purposes of prediction
for (i in 1:8){
  print(paste0("coeff ", i, " ", round(mean(eg0_2a$coeff[[1]][,i]),3)))
}
# "coeff 1 -1.039" b[1]
# "coeff 2 -0.152" b[2]
# "coeff 3 -0.073" b[3]
# "coeff 4 -3.984" b0[1]
# "coeff 5 -0.213" b0[2]
# "coeff 6  0.041" b0[3]
# "coeff 7  1.553" d
# "coeff 8  0.002" sigma
```

*FIG. 5J*

DECISION SUPPORT SYSTEMS FOR DETERMINING CONFORMITY WITH MEDICAL CARE QUALITY STANDARDS

CROSS-REFERENCE TO RELATED APPLICATIONS

This application claims the benefit of U.S. Provisional Application No. 62/395,365, titled "PREDICTING CONFORMITY TO MEDICAL CARE QUALITY STANDARDS," filed on Sep. 15, 2016, which is hereby expressly incorporated by reference in its entirety.

BACKGROUND

With respect to health services finance, accurate and reliable quality measurement is increasingly important to public-sector federal and state payment strategies and to private-sector commercial payment strategies as well. A new generation of technical infrastructure is enabling payers in both sectors to define and identify high-value service delivery. Recent reforms, including the Affordable Care Act of 2010, are pushing payers to become more prudent purchasers of care, spurring them to implement payment strategies that reward value in the health care system.

The U.S. federal Medicare program, despite its historical reputation of being a payer with little regard to the value of the services it buys, has recently put in place a range of programs aimed at assessing quality and value, coupled with financial incentives for those whose assessments indicate superior performance and financial penalties for those whose performance is inferior or falls below normative target levels. Such programs are called 'Pay for Performance' (P4P) or 'Pay for Value' (P4V) programs. More such programs are expected to be forthcoming. The issues surrounding these programs are complex, and it is no surprise that there is a level of contention between providers and regulators and payors, even though all parties profess committedness to improved health services quality. Participation in all Clinical Quality Measures (CQM) programs is, to date, voluntary. However, a decision not to participate increasingly carries a financial penalty, as payors try to encourage behavior they cannot force.

Various jurisdictions are becoming increasingly sensitive to their annual spending on health services, to the opportunities to offset those expenditures with improvements in quality and safety and other aspects of value, and to the need for health information technology (health IT) in order to fully leverage those opportunities. And, like other health care providers exploring health IT implementation, they are weighing whether to participate in the incentive programs to promote adoption of electronic health record (EHR) systems, which are commonly referred to as "meaningful use" ('MU'). MU is the linchpin of the Medicare and Medicaid EHR Incentive Programs, established under the U.S. Health Information Technology for Economic and Clinical Health (HITECH) Act, enacted as part of the American Recovery and Reinvestment Act of 2009. Providers demonstrate meaningful use by "attesting" to certain criteria for different stages of MU, and the attestations may be audited to determine the veracity of the attestations.

The U.S. Tax Relief and Health Care Act of 2006 required the establishment of a quality reporting system for eligible health care professionals, incorporating an incentive payment for those who satisfactorily report data on quality measures for covered professional services furnished to Medicare beneficiaries. Though the Centers for Medicare & Medicaid Services (CMS) named it the Physician Quality Reporting Initiative (PQRI), eligible professionals also include physician assistants, advanced practice registered nurses, licensed social workers, clinical psychologists, and others such as speech and physical therapists. Under the Patient Protection and Affordable Care Act of 2010 (ACA), there was a name change to the Physician Quality Reporting System (PQRS).

By 2015, there were 300 individual measures established in the U.S. The U.S. Centers for Medicare & Medicaid Services (CMS) allow (but do not compel) physician groups of at least 200 eligible professionals filing under the same tax identification number to report as groups rather than as individuals. The number of measures and the scope of quality assessment continue to be expanded each year. The measures and normative target levels for each measure are curated by various 'steward' organizations such as the National Quality Foundation (NQF), the Joint Commission on Accreditation of Health Organizations (JCAHO), the National Committee for Quality Assurance (NCQA), and others. While manual, paper-based reporting of providers' performance according to each applicable Clinical Quality Measure is still permitted, increasingly most providers are utilizing electronic methods for reporting, wherein their performance results are computed from data retrieved from online electronic health records (EHR) systems. Such computer-based online calculation and reporting methods are termed Electronic Clinical Quality Measures (eCQM).

The CQM, eCQM, P4P, and P4V measures, or MU measures and similar performance measures are an aspect of health care reform wherein a diverse array of clinical safety and effectiveness measures relating to clinical processes and outcomes are utilized to financially incentivize the delivery of health services in such a way as to achieve desirable clinical outcomes via efficacious processes, toward the improvement of individual benefits and societal value from the care services rendered.

However, the methods and technologies utilized for determining conformity to these measures suffer from imprecision, unreliability, and inaccuracy. That is, while attempts have been made to provide a technological solution to improve decision support systems to overcome these deficiencies, conventional technology has generally failed to provide a reliable and accurate solution. As such, what is needed are enhanced systems and methods to address the deficiencies of prior technologies provided for in the described embodiments.

SUMMARY

A technology is provided for accurately estimating conformity to Clinical Quality Measures (CQM) or Electronic Clinical Quality Measures (eCQM), Pay-for-Performance (P4P) measures or Pay-for-Value (P4V) measures, or Meaningful Use (MU) measures in human health care delivery. For example in one embodiment, an apparatus utilizes Bayesian Markov Chain Monte Carlo (BCMC) statistical methods to achieve reliable estimates for such measures despite the small subgroup sample sizes accruing during each measurement period. Further, in some embodiments, the apparatus utilizes zero- and one-inflated beta regression that is robust against moderate prevalence of zero or one counts in the numerators for such measurements and determinations of statistical associations with such factors as clinician, care venue, and patient attributes.

Accordingly, in an embodiment as will be further described herein, patient data is measured and received for patients meeting an inclusion-exclusion criteria for the measurement period for each of the facilities and treating clinicians. Clinician data for provider clinicians who provided the services to said patients is also accessed and received. Next, numerator and denominator counts are constructed from the patient and provider clinician data in order to calculate percentages or rates or other eCQM, MU, or P4P measures. Attribute variables to be included in statistical models of eCQM, MU, or P4P performance are selected and the attribute variables' values for the patients and provider clinicians are assembled. Next a Bayesian Markov Chain Monte Carlo (MCMC) zero-inflated or one-inflated beta regression is initiated. In an embodiment, the Bayesian MCMC process uses a Gibbs Sampler, or other suitable sampling method, by first performing a 'burn-in' series of iterations from which the sampled distribution values are discarded. Further iterations are determined from the Bayesian MCMC process until model convergence is achieved. In some instances, the sampled distribution values may be altered by a negligible amount by additional iterations. The results from the further iterations for stored for further analysis.

Next, from the converged model, the regression coefficients and beta distribution parameters are extracted, and those regression coefficients and distribution parameters having statistical significance (e.g., $p<0.05n$ or other criterion) are identified. The clinicians' conformity (or not) with the eCQM or MU or P4P measures, and the corresponding statistical associations (if any) with the attributes of the patients, the providers, or the facilities where services were rendered (or other factors, according to which regression coefficients, if any, are statistically significant) may be communicated to the provider clinicians or to the organization's management.

In one aspect, an embodiment of this disclosure describes techniques for facilitating analysis of information relating to medical treatments delivered to patients. Embodiments are said to facilitate the analysis of information because they are capable drawing critical and improved determinations relating to medical treatments delivered to patients—determinations that conventional technology has been incapable of discerning or recognizing based on the limitations of their conventional implementation. Data is received from multiple data sources. For example, data can be received from one or more electronic health record (EHR) systems and one or more other sources of data. The data received from the data sources may provide information about patients in a population who have received one or more therapies. Patient-centric records may be generated at one or more computing devices. Each of the patient-centric records comprises patient data regarding a different patient in the population. The patient data in the patient-centric records is based on the data received from the data sources.

In another aspect, an embodiment of this disclosure relates to techniques for analyzing a set of patient data with a computing device to estimate a care process measure or a post-treatment outcome. Disclosed are techniques for modeling the conformity to target process and outcomes measures in a patient population based on zero-inflated and/or one-inflated Markov Chain Monte Carlo Bayesian beta regression on subsets of the patient population. The techniques include using the computing device to compare the distribution of baseline characteristics of a population subset with the distribution of baseline characteristics in the entire population. Based on this comparison, the distribution of therapy outcomes in the population subset may be modified according to the distribution of baseline characteristics of the entire population in order to model the distribution of outcomes for the entire population. Such techniques may be used to account for important differences in the distribution of baseline characteristics of a population subset as compared to the entire population of patients.

Accordingly, embodiments provide for new and improved decision support technology to solve the problems associated with the conventional industry implementations, thereby providing enhanced decision support systems and methods. The decision support systems are said to be enhanced since they achieve determinations and results that have not been possible using prior technological solutions. That is, prior technological solutions were generally incapable of providing improved determinations that are achieved by employing the embodiments described herein.

BRIEF DESCRIPTION OF THE DRAWINGS

The present invention is described in detail below with reference to the attached drawing figures, wherein:

FIG. 3 depicts a table of example numerator and denominator counts for an embodiment of this technology reduced to practice;

FIGS. 5A-5J illustratively provide an example embodiment of a computer program routine for determining eCQM conformity fraction NQF 0004b and statistical confidence intervals for groups and individuals of patients.

DETAILED DESCRIPTION

Figure 1A:
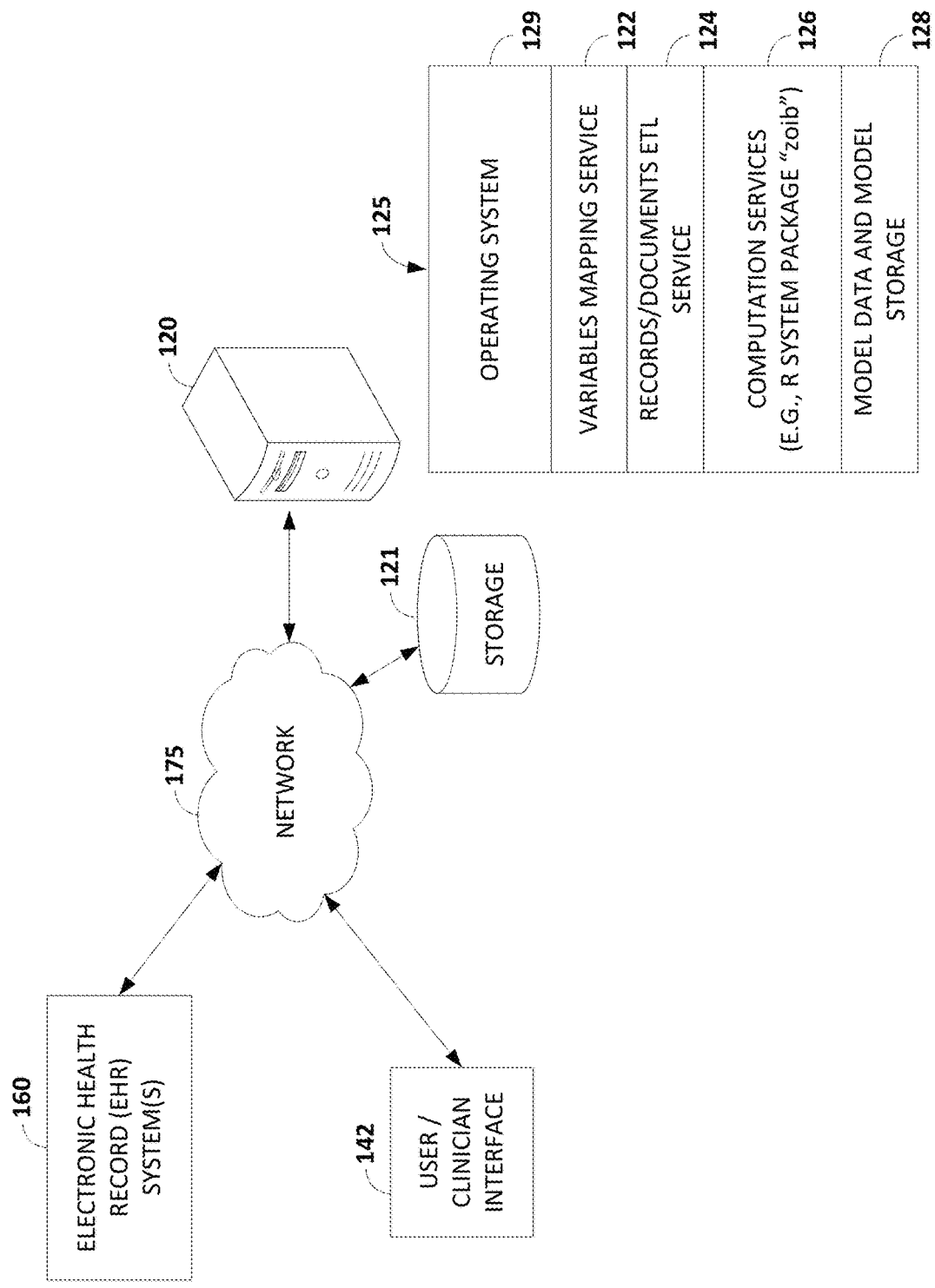
FIGS. 1A and 1B depict aspects of an illustrative architecture suitable for practicing an embodiment of the invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media. As such, computer readable media may be specifically purposed or specially programmed to employ the specific techniques and logical structures described herein. Upon being specifically programmed according to embodiments described in the present application, the computer readable media may provide for enhanced decision support systems that are capable of generating improved determinations that were previously unattainable using conventional computers.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or storage devices. These technologies can store data momentarily, temporarily, or permanently.

As described above, accurate and reliable quality measurement is increasingly important to public-sector federal and state payment strategies and to private-sector commercial payment strategies. The CQM, eCQM, P4P, and P4V and similar performance measures are an aspect of health care reform wherein a diverse array of clinical safety and effectiveness measures relating to clinical processes and outcomes are utilized to financially incentivize the delivery of health services in such a way as to achieve desirable clinical outcomes via efficacious processes, toward the improvement of individual benefits and societal value from the care services rendered.

'Meaningful Use' (MU) measures are one component of this aspect of health reform. 'Meaningful Use' measures generally refer to performance metrics that are used in ascertaining clinical outcomes, effectiveness, or process quality associated with clinicians' utilization of electronic health record (EHR) systems that are intended to support evidence-based best care practices, lower variability or inconsistency in care content, and the ability to measure attributes of the care delivered so as to establish accountability for that care, which in turn can be a basis for payment incentives and penalties for superior and inferior care quality, respectively. In other words, 'Meaningful Use' measures refer to the context of using EHR software systems to conduct and document the process of care delivery. The establishment of eCQM and P4P and MU measures for mental health and addiction medicine was a late addition to health care reform regulations in the U.S.

In general, eCQM and P4P and MU are salutary policies with a variety of quality and safety benefits for the public health. However, the fact that some disciplines, such as alcoholism and drug addiction treatment are often "one-time" treatments and tend to experience relatively modest numbers of newly-incident patients per year and the clinicians who treat these patients may not have multi-year longitudinal engagement with these patients means that the accuracy and statistical reliability of the measures may not be as stable and fair as is the case for other chronic medical ambulatory care sensitive conditions ("ACSCs") such as asthma or hypertension or hyperlipidemia or heart failure or diabetes, all of whose management involves numerous episodes of care provisioned over periods of multiple years and whose management is never "one-time" treatment.

However, conventional technologies have generally failed to provide an adequate solution for determining conformity of outcomes with these performance metrics and what attributes of a patient or group of patients may cause a lack of conformance One significant limitation of conventional approaches related to measuring conformity to outcomes, effectiveness, or process quality measures or to MU measures in such a case is that (1) aggregating the population into one large category or grouping impairs the ability to analyze the results to determine the factors that are statistically associated with conformity or lack thereof. One often needs instead to preserve the detail of each combination of factor values, where factors may be (but are not limited to) values of age, gender, treatment location, treating clinician, comorbid conditions, history of treatments received, prescribed treatment frequency, prescribed treatment duration, treatment cost, adherence to prescribed treatment, services utilization intensity, health plan or payor, indication for treatment (including employer-mandated and court-ordered), ethnicity, annual income, employment status, education level, criminal justice or incarceration history, and marital status. As such, using the enhanced decision support technology described herein overcomes the limitations associated with the conventional approach, which cannot be overcome by simply using a computer. Rather, embodiments overcome these limitations by employing new techniques to generate determinations with a higher degree of accuracy and efficiency.

An additional significant limitation of conventional approaches related to measuring efficaciousness of care or conformity to target metrics thresholds to determine incentives or penalties is that (2) the results for individual clinicians can seem numerically unstable or capricious from measurement period to measurement period, such that clinicians become frustrated and despair of receiving fair and just payments for their services. In the U.S., this is resulting in many clinicians' early decisions to retire or to exit clinical practice to seek employment in other lines of work, so that the labor force of clinicians is experiencing unnatural attrition and shortages of clinicians in many areas are occurring. This effect is contrary to the public health interest, and would thwart the intent and public health motivations of the health reform legislation that produced the CQM-related programs. Although there is not yet adequate evidence to assess, it is possible as well that context-agnostic 'one-size-fits-all' eCQM or P4P or MU measures and corresponding overly simplistic 'one-size-fits-all' health services processes may result in reduced patient retention or reduced patient adherence to the prescribed plan of care. Such an effect would likewise thwart the intended purpose of the health reform initiatives.

Thus, a principal aim of the analysis of per-period performance data is to discover whether or not the different rates of conformity to target quality measures established under MU or P4P or similar programs or regulations are statistically associated with clinic location, age, gender, and/or clinician or other factors. A secondary aim of the analysis is to inform management decisions regarding what corrective actions or improvements to undertake based on said associations. If no associations are discovered, then there is no objective evidence for or against undertaking actions based on any of the factors. That outcome itself may constitute a valuable finding of fact, inasmuch as it would prevent expensive actions that would likely be fruitless or yield little benefit.

The fact of the matter is that, on a detailed 'clinician-clinic location-age category-gender' basis, the number of persons accruing during each measurement time period is quite small, often ranging from 10 to several dozen individuals. These are the counts that form the denominator population for the calculation of percentages conforming to the quality criterion. The small-count nature of these accruals typically confounds conventional decision support systems.

Further, the small-count nature of these accruals is exacerbated insofar as some of the MU and P4P measures have arbitrarily established very narrow age-range categories, especially when addressing quality of care in pediatric age groups. For example, in addiction medicine one of the categories is patients between the ages of 13 and 17, inclusive. By definition, the numerator counts are strictly smaller than the denominator counts and, among these, one obtains many numerators that are either 0 or 1 when one analyzes detailed 'clinician-clinic location-age category-gender' groups.

Taken together, based on the uniqueness of the accruals to be analyzed, and the limitations associated with doing so, new techniques and logical structures are required. Conventional methods and systems are largely inadequate. As mentioned, the disadvantages of conventional technology cannot be overcome by simply using a computer. This is because there are no known methods or systems that are capable of achieving the results of the current embodiments, even if employed by a computer. Accordingly, the problems with the conventional technology require new and improved techniques and logical structures that specifically overcome these drawbacks. Hence, the embodiments described herein are meant to address these disadvantages by implementing new and improved techniques and features that are not currently implemented in conventional technology. In this way, the embodiments described herein provide enhanced decision support systems that are capable producing more reliable and accurate determinations that have not yet been achieved.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, example operating environment 100 provides an aspect of a computerized system for compiling and/or running aspects of this disclosure including collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Environment 100 includes one or more electronic health record (EHR) systems, such as hospital EHR system 160, communicatively coupled to network 175, which is communicatively coupled to computer system 120. In some embodiments, components of environment 100 that are shown as distinct components may be embodied as part of or within other components of environment 100. For example, EHR systems 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in computer system 120. Similarly, EHR system 160 may perform functions for two or more of the EHR systems (not shown). In an embodiment, EHR system 160 includes historical claims data for health services, apportionment data, and related health services financial data.

In some embodiments of the disclosure, sequence itemset mining is performed using data about a population of patients derived from patient EHR information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system 160 include one or more data stores of health records, which may be stored on storage 121, and may further include one or more computers or servers that facilitate the storing and retrieval of the health records. In some embodiments, EHR system 160 may be implemented as a cloud-based platform or may be distributed across multiple physical locations. EHR system 160 may further include record systems, which store real-time or near real-time patient (or user) information, such as wearable, bedside, or in-home patient monitors or sensors, for example.

Example operating environment 100 further includes provider user/clinician interface 142 communicatively coupled through network 175 to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient, set of patients, or provider clinicians, according to the embodiments presented herein. Embodiments of interface 142 also facilitates accessing and receiving information from a user or health care provider about a specific patient or population of patients including patient history; health care resource data; variables measurements, timeseries, and predictions (including plotting or displaying the determined outcome and/or issuing an alert) described herein; or other health-related information, and facilitates the display of results, recommendations, or orders, for example. In an embodiment, interface 142 also facilitates receiving orders for the patient from the clinician/user, based on the results of monitoring and predictions. Interface 142 may also be used for providing diagnostic services or evaluation of the performance of various embodiments.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on interface 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or a computing device running interfaces 140 and 142. In some embodiments, interface 142 operates in conjunction with software stack 125.

In embodiments, variables mapping service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages including package zoib used for Bayesian Inference for Beta Regression and Zero-or-One Inflated Beta Regression, natural language processing services (not shown) such as Discern nCode™ developed by Cerner Corporation, or similar services. In an embodiment, computation services 126 include the services or routines, which may be embodied as one or more software agents or routines such as the example embodiments of computer program routines illustratively provided in FIGS. 5A-5J. In some embodiments, computation services 126 use EHR 160 and/or model data and model storage services 128. Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
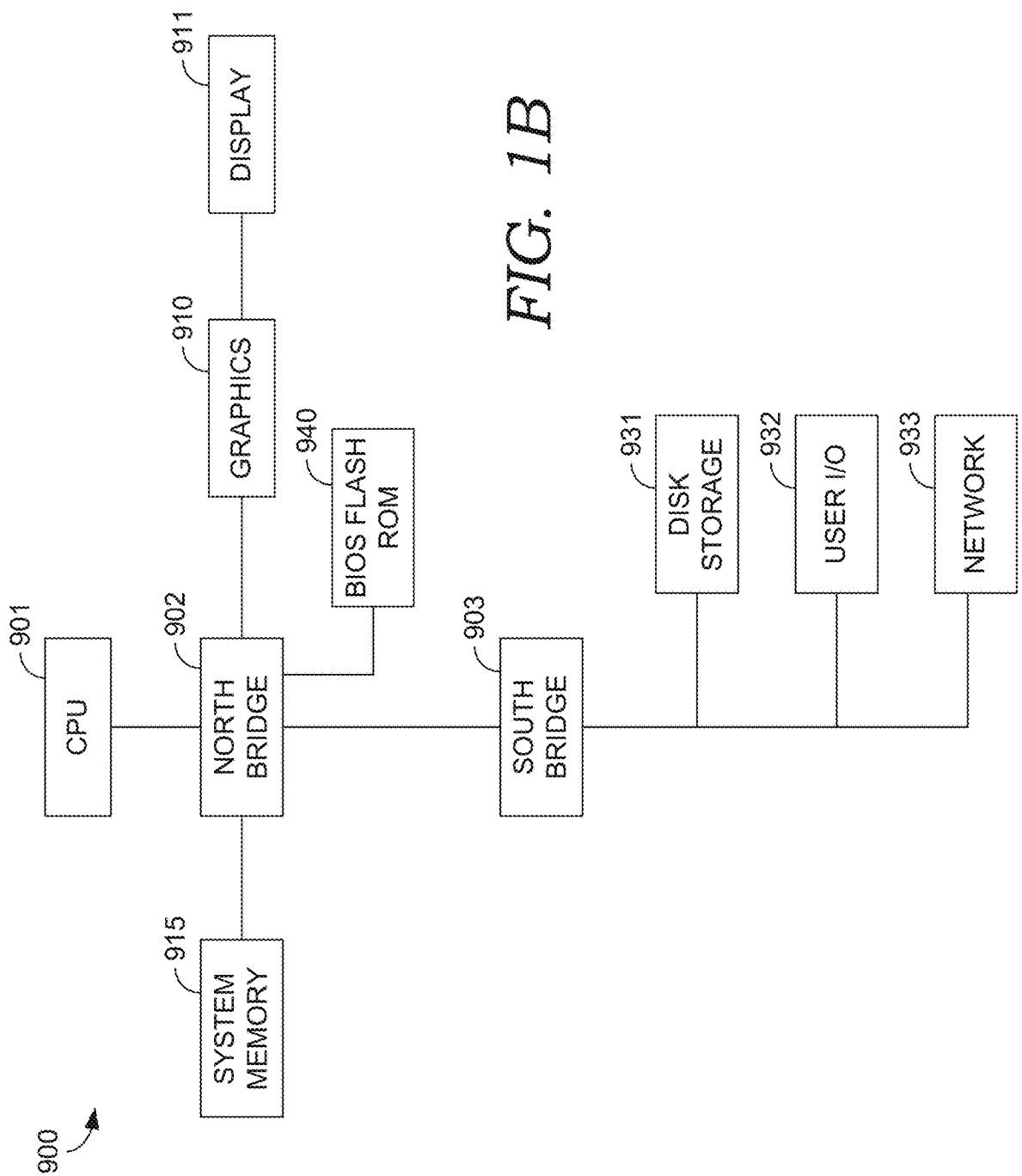

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
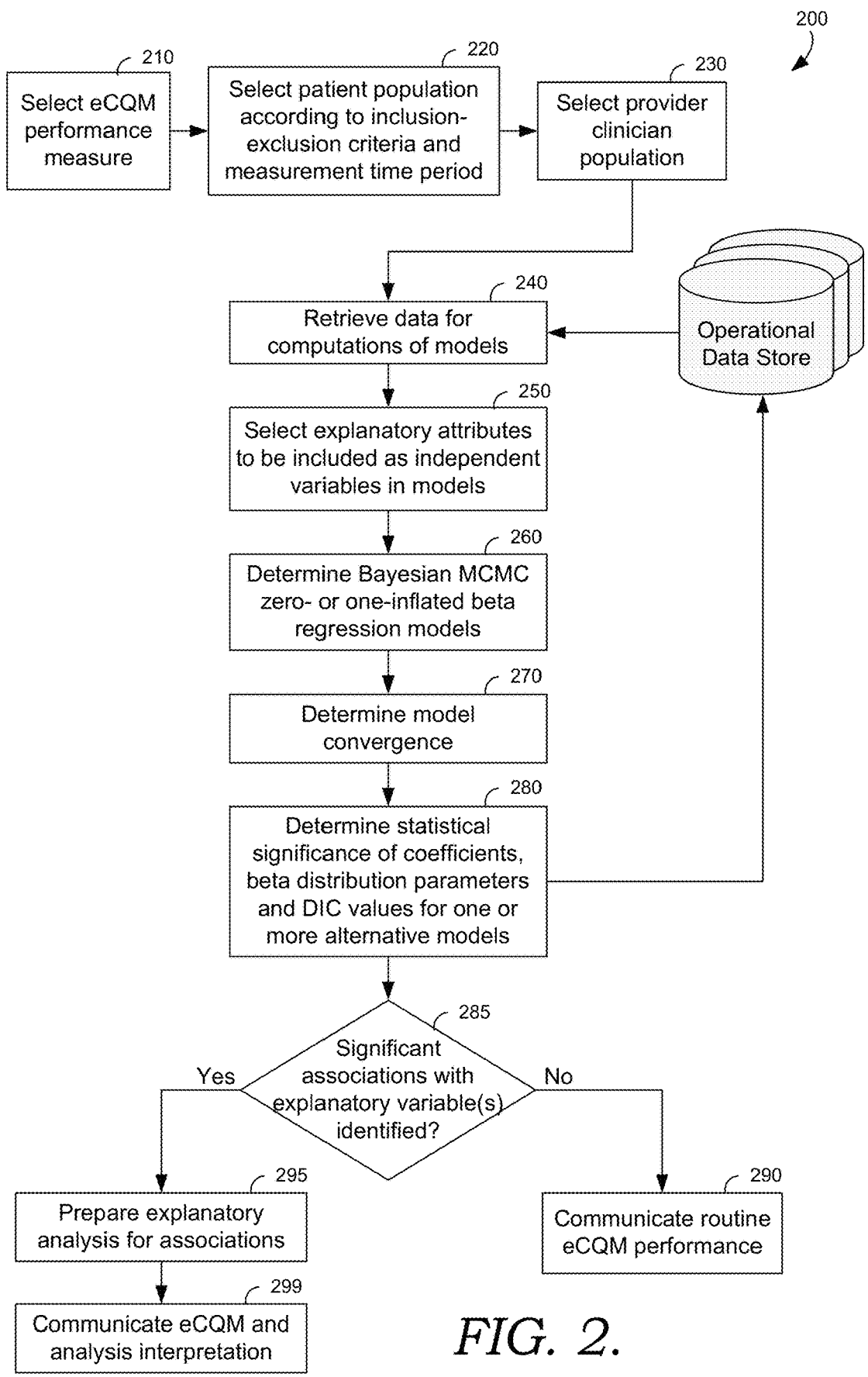
FIG. 2 depicts a flow diagram of an exemplary method for determining conformity to medical care performance measurements by performing zero-inflated and/or one-inflated beta regression on the dataset using Bayesian Markov Chain Monte Carlo methods.

With reference now to FIGS. 2, 3, 4A and 4B, and 5A-5J, a flow diagram is provided in FIG. 2 illustrating a method 200 for determining conformity to medical care performance measurements by performing zero-inflated and/or one-inflated beta regression on the dataset using Bayesian Markov Chain Monte Carlo analysis. Aspects of an embodiment reduced to practice using method 200 are illustratively provided in FIGS. 3, 4A-4B, and 5A-5J, which include respectively: a table of example numerator and denominator counts and percentages (by clinician-clinic-age-category-gender); examples of model prediction vs. observation of eCQM conformity from the embodiment reduced to practice based on the computer program routine of FIGS. 5A-5J; and a computer program routine for determining eCQM conformity fraction NQF 0004b and statistical confidence intervals for groups and individuals of patients.

Accordingly and at a high level, in one aspect, this disclosure describes techniques and logical structures for facilitating analysis of information relating to medical treatments delivered to patients. Data is received from multiple data sources. For example, data can be received from one or more electronic health record (EHR) systems and one or more other sources of data. The data received from the data sources may provide information about patients in a population who have received one or more therapies. Patient-centric records may be generated at one or more computing devices. Each of the patient-centric records comprises patient data regarding a different patient in the population. The patient data in the patient-centric records is based on the data received from the data sources.

In another aspect, this disclosure provides techniques for analyzing a set of patient data with a computing device to estimate a care process measure or a post-treatment outcome. In particular, disclosed are techniques for modeling the conformity to target process and outcomes measures in a patient population based on zero-inflated and/or one-inflated Markov Chain Monte Carlo Bayesian beta regression on subsets of the patient population. The techniques include using the computing device to compare the distribution of baseline characteristics of a population subset with the distribution of baseline characteristics in the entire population. Based on this comparison, the distribution of therapy outcomes in the population subset may be modified according to the distribution of baseline characteristics of the entire population in order to model the distribution of outcomes for the entire population. Such techniques may be used to account for important differences in the distribution of baseline characteristics of a population subset as compared to the entire population of patients.

In one example, a method facilitates analysis of outcomes of medical or surgical or behavioral therapies. The method comprises receiving data from multiple data sources. The data from the data sources provides information about patients in a population. Each of the patients in the population has received one or more of the therapies. The method also comprises generating patient-centric records in a computing device. Each of the patient-centric records comprises patient data regarding a different patient in the population. The patient data of the patient-centric records is based on the data received from the data sources.

In another example, a computing device comprises a data storage system that stores instructions. The computing device also comprises a processing system coupled to the data storage system. The processing system reads the instructions from the data storage system and executes the instructions. Execution of the instructions by the processing system causes the computing device to generate patient-centric records. Each of the patient-centric records comprises patient data regarding a different patient in a population. The patient data of the patient-centric records is based on data received from multiple data sources. The data from the data sources provides information about the patients in the population. Each of the patients in the population has received one or more therapies.

In yet another example, a computer storage medium stores instructions. Execution of the instructions by a processing system of a computing device causes the computing device to generate patient-centric records. Each of the patient-centric records comprises patient data regarding a different patient in a population. The patient data of the patient-centric records is based on data received from multiple data sources. Each of the patients in the population has received one or more therapies.

In yet another example, a computing device comprises means for receiving data from multiple data sources. The data from the data sources provides information about providers delivering services in a health system. Each of the provider clinicians has provided one or more of the therapies. The computing device also comprises means for generating provider-centric records. Each of the provider-centric records comprises provider data regarding a different provider in the health system. The provider data of the provider-centric records is based on the data received from the data sources.

Accordingly, aspects of this disclosure describe techniques and logical structures for facilitating analysis of information relating to one or more therapies. Such techniques can include receiving data from multiple data sources. The data may provide information about patients who have received one or more medical or surgical or behavioral therapies. Furthermore, such techniques may include using the data to generate therapy-centric records. The therapy-centric records may be used to perform analysis operations that generate information about the processes or outcomes of the therapies. For example, the analysis operations may be applied to draw inferences with respect to outcomes of behavioral therapies—inferences that conventional technology has largely failed to generate based on its conventional approach. In another example, the analysis operations may be applied to draw inferences regarding therapy delivery based on more detailed data regarding patients and provider clinicians. As will be described, the techniques described may be performed, in whole or in part, by one or more computing devices configured to support the techniques. While one or more computing devices may be used, the improvement is not realized by simply using a computer. Rather, the improvement is realized through the improved systems and methods described herein, which are specifically designed to overcome the challenges associated with drawing reliable determinations from the specific type of data being analyzed. As mentioned, the specific type of data being analyzed confounds conventional technology, rendering conventional technology generally inadequate. As such, the current embodiments result in a significant improvement over conventional technology.

Modeling the distribution of outcomes in a patient population based on the distribution of the outcomes in a subset of the patient population uses data representing the distribution of baseline characteristics of a population subset relative to the distribution of baseline characteristics in the entire population. Based on a comparison of the relative distribution of baseline characteristics of a population subset, the distribution of therapy outcomes in the population subset may be modified according to the distribution of baseline characteristics of the entire patient population. Such techniques may be used to account for important differences in the distribution of baseline characteristics in a population subset as compared to the entire population of patients. In addition, techniques for modeling the distribution of outcomes in a patient population served by a health delivery system in which various providers are engaged in delivering health services are provided by some embodiments.

In some embodiments, baseline characteristics may include information known or knowable prior to a medical therapy or other intervention that is to be studied. When the intervention is a medical therapy, for example, the baseline characteristics include information, such as patient or provider clinician or therapy characteristics, known or knowable prior to the initiation of the therapy.

In addition, in some embodiments, the computing device accesses a data storage system storing an indication of an association between at least one aspect of the baseline characteristics and at least one of the outcomes in the subset of the population. As referred to herein, an association may be any relationship between two characteristics that renders them statistically dependent. In one example, a computing device may analyze the outcomes along with baseline characteristics for the subset of the population to find the association between at least one aspect of the baseline characteristics and at least one of the outcomes in the subset of the population. In another example, the computing device may access a previously determined indication of the association between at least one aspect of the baseline characteristics and at least one of the outcomes in the subset of the population. For example, once the association has been determined, it may not be necessary to analyze updated or new data sets to verify or model a known association.

Turning now to FIG. 2 and method 200 for performing zero-inflated and/or one-inflated beta regression on the dataset using Bayesian Markov Chain Monte Carlo. In statistics, Markov chain Monte Carlo (MCMC) methods are a class of methods for sampling from a probability distribution based on constructing a Markov chain that has the desired distribution as its equilibrium distribution. The state of the chain after a number of steps is then used as a sample of the desired distribution. The quality of the sample improves as a function of the number of steps or iterations. Gibbs sampling or a Gibbs sampler is a Markov chain Monte Carlo (MCMC) method for obtaining a sequence of observations which are approximated from a specified multivariate probability distribution (i.e. from the joint probability distribution of two or more random variables), when direct sampling is difficult. This sequence can be used to approximate the joint distribution (for example, to generate a histogram of the distribution); to approximate the marginal distribution of one of the variables, or some subset of the variables (for example, the unknown parameters or latent variables); or to compute an integral (such as the expected value of one of the variables). Typically, some of the variables correspond to observations whose values are known, and hence do not need to be sampled. Gibbs sampling may be used as a means of statistical inference such as Bayesian inference.

Bayesian analysis is a statistical analysis that answers research questions about unknown parameters of statistical models by using probability statements. Bayesian analysis rests on the assumption that all model parameters are random quantities and thus can incorporate prior knowledge. This assumption is in sharp contrast with the more traditional, also called frequentist, statistical inference where all parameters are considered unknown but fixed quantities. Bayesian analysis follows a simple rule of probability, the Bayes rule, which provides a formalism for combining prior information with evidence from the data at hand. The Bayes rule is used to form the so called posterior distribution of model parameters. The posterior distribution results from updating the prior knowledge about model parameters with evidence from the observed data. Bayesian analysis uses the posterior distribution to form various summaries for the model parameters including point estimates such as posterior means, medians, percentiles, and interval estimates such as credible intervals. Moreover, all statistical tests about model parameters can be expressed as probability statements based on the estimated posterior distribution.

If one aims to estimate the probability that the parameter of interest belongs to some pre-specified interval, one requires a Bayesian framework, because this probability cannot be estimated within the frequentist framework. The universality of the Bayesian approach is probably its main methodological advantage to the traditional frequentist approach. Bayesian inference is based on a single rule of probability, the Bayes rule, which is applied to all parametric models. This makes the Bayesian approach universal and greatly facilitates its application and interpretation. The frequentist approach, however, relies on a variety of estimation methods designed for specific statistical problems and models. Often, inferential methods designed for one class of problems cannot be applied to another class of models. Bayesian methods are particularly suited to computations of proportions, rates, incidence, or prevalence.

In Bayesian analysis, we can use previous information, either belief or experimental evidence, in a data model to acquire more balanced results for a particular problem. For example, incorporating prior information can mitigate the effect of a small sample size. Importantly, the use of the prior evidence is achieved in a theoretically sound way. By using the knowledge of the entire posterior distribution of model parameters, Bayesian inference is more comprehensive and flexible than the traditional frequentist statistical inference. Bayesian inference is exact, in the sense that estimation and prediction are based on the posterior distribution. The latter is either known analytically or can be estimated numerically with an arbitrary precision. In contrast, many frequentist estimation procedures such as maximum likelihood rely on the assumption of asymptotic normality for inference.

Zero-inflated and one-inflated models are designed to deal with situations where there is an "excessive" number of individuals with a count of 0 or 1, respectively. Zero-inflated and one-inflated models are important when statistical models fit the data poorly as indicated by Deviance Information Criterion (DIC), or Akaike Information Criterion (AIC), or likelihood ratio or other test. For example, a Poisson regression model often fits the data poorly, as indicated by a DIC or other test. That is because the Poisson model assumes that the conditional variance of the dependent variable is equal to the conditional mean. In most count data sets, the conditional variance is greater than the conditional mean, often much greater, a phenomenon known as overdispersion.

The zero-inflated Poisson (ZIP) model is one way to allow for overdispersion. This model assumes that the sample is a "mixture" of two sorts of individuals: one group whose counts are generated by the standard Poisson regression model, and another group (call them the absolute zero group) who have zero probability of a count greater than 0. Observed values of 0 could come from either group. Although not essential, the model is typically elaborated to include a logistic regression model predicting which group an individual belongs to. In cases of overdispersion, the ZIP model typically fits better than a standard Poisson model, as evaluated by AIC or BIC statistics. And it's a much simpler model to estimate and interpret. So if the choice is between a ZIP model and a negative binomial model, the latter tends to yield goodness-of-fit results that are superior to the former. In turn, a zero-inflated negative binomial (ZINB) model often yields a better fit than a conventional negative binomial model regression model. In the present invention, Baysian MCMC regressions are performed with percentages or rates as the dependent eCQM or P4P or MU variable, where the percentages or rates are calculated from numerator and denominator 'count' data and follow a beta distribution.

Situations where a zero-inflated model is preferred include when the dependent variable is number of children ever born prematurely to a sample of women 40 years of age and older. It is reasonable to suppose that a considerable proportion of women in this age group postmenopausal and are biologically unable to have children. For these women, no variation on the predictor variables (whatever they might be) could change the expected number of children or the rate of preterm births.

In the case of addiction and other drug (AOD) conditions, a zero-inflated model is advantageous when the dependent variable is the number of patients receiving N treatment episodes within a defined timeframe in the care of a sample of mental health provider clinicians, where N>1. It is reasonable to suppose that some clinicians are engaged to provide triage and initial care in a single episode N=1 and to refer or arrange care by others for subsequent visits. For such a clinician, no variation on the predictor variables (whatever they might be) could change the expected number of visits handled by that clinician or the rate of multiple treatment episodes.

Accordingly, method 200 begins at step 210; select eCQM performance measure, patient population according to inclusion-exclusion criteria and measurement time period (step 220), and provider clinician population (step 230) who provided the services to the patients of step 220. Some embodiments of step 220 further include measuring the patient data for the patients meeting the inclusion-exclusion criteria for the measurement time period for each of the facilities and treating clinicians. At step 240, retrieve the patient and provider clinician data corresponding to the selections of steps 220 and 230. Some embodiments of method 200 also may construct numerator and denominator counts from the patient and provider clinician data for the purpose of calculating percentages or rates or other eCQM, MU, or P4P measures. An example of such numerator and denominator counts is illustratively provided in FIG. 3.

At step 250, select explanatory attributes to be included as independent variables in the models. Embodiments of step 250 may include determining or selecting attribute variables to be included in statistical models of eCQM, MU, or P4P performance, and assembling attribute variables' values for the patients and provider clinicians. At step 260, Bayesian MCMC zero- or one-inflated beta regression models are determined. Embodiments of step 260 initiate Bayesian Markov Chain Monte Carlo (MCMC) zero-inflated or one-inflated beta regression. In an embodiment, a Gibbs Sampler or other suitable sampling method is utilized, by first performing a 'burn-in' series of iterations from which the sampled distribution values are discarded. Some embodiments of step 260 may be performed using the zoib R-package of software services 126 (described in connection to FIG. 1A) as illustratively shown in FIG. 5A-5J. In particular, aspects of method 200, including step 260, may be carried out using the computer program provided in FIGS. 5A-5J.

At step 270, Bayesian MCMC zero-inflated or one-inflated beta regression, which may use Gibbs Sampling in an embodiment, continues for further iterations until model convergence is determined. In some embodiments, the sampled distribution values may be altered by a negligible amount by additional iterations, and the results from the further iterations for stored for further analysis. At step 280, determine statistical significance of coefficients, beta distribution parameters and DIC values for one or more alternative models. In some embodiments of step 280, from the converged model, the regression coefficients and beta distribution parameters are extracted, and those regression coefficients and distribution parameters having statistical significance (e.g., $p<0.05n$ or other criterion) are identified.

At step 285, if there is not statistically significant associations with explanatory variables, then at step 290, an indication may be provided (such as a communication) that eCQM performance is routine. But if statistically significant associations with explanatory variables is determined, then method 200 proceeds to step 295 and an explanatory analysis for the associations is determined. In one embodiment, a computer-performed analysis is performed to interpret the differences and may be provided to a clinician in order to explain the differences. The analysis may indicate conformity (or nonconformity) to the eCQM or MU or P4P measures, and may further include an indication of the degree of nonconformity. In one embodiment, the analysis includes an indication of the difference(s) such as a statistical deviation or numerical expression representing the difference. At step 299, the eCQM analysis and an interpretation (if performed) is provided to a provider clinician, to an organization's management the clinicians, or other user(s). For example, in an embodiment, a clinicians' conformity (or not) with the eCQM or MU or P4P measures, and the corresponding statistical associations (if any) with the attributes of the patients, the providers, the facilities where services were rendered (or other factors, according to which regression coefficients, if any, are statistically significant) may be communicated to the provider clinicians or to the organization's management.

Some embodiments of method 200 accommodate boundary inflations at 0 or 1 values of the response variable(s). These embodiments model clustered and correlated responses by introducing random components into the linear predictors of the regression link functions. The inferences from the models are based in the Bayesian framework via Markov Chain Monte Carlo (MCMC) methods such as randomized Gibb Sampling over a plurality of iterations. In an embodiment, at least several thousand iterations are performed from which results are retained, subsequent to an initial "burn-in" series of iterations from which results are discarded.

In one embodiment, the decision support system can send a notification (such as an alert or other indication) through network 175 upon determining there are attributes of a patient population that contribute to its nonconformity to performance standards. The notification may comprise the communication of the eCQM and analysis interpretation (e.g., the determination made at step 299) along with a recommendation (e.g., a recommendation as to the conformity of a set of patient attributes 610). The notification be communicated through a call, HTTP, SMS text-message, or other form of electronic or radiofrequency communication, and may include a link to a web-based interface similar to the graphical user interface described with reference to FIG. 6. Additionally, the notification and the associated recommendation may be received and reviewed without an entity having to actively monitor the patient data. This provides further advantages over conventional systems and methods since conventional technology was generally unable to provide these notifications based on their inability to generate reliable determinations.

In one embodiment, policies or recommendations to remedy the nonconformity of any particular attribute of patients for a given entity may be provided to a user. That is, embodiments may provide recommendations of policies or changes from entities that are known to statistically conform to performance standards for that particular attribute. For instance, enhanced decision support systems may automatically or autonomously retrieve data for a particular entity, employ specific techniques to detect nonconformance, determine there is a nonconformance, and notify the entity's representative of the nonconformance and provide further solutions for addressing the nonconformance. The notification may include the policies or methods of other entities that the decision support system has identified as statistically conforming to performance standards. As such, by employing the improved methods and systems, health care entities can now be made aware of the particular attributes of a population that impact conformance.

Figure 6:
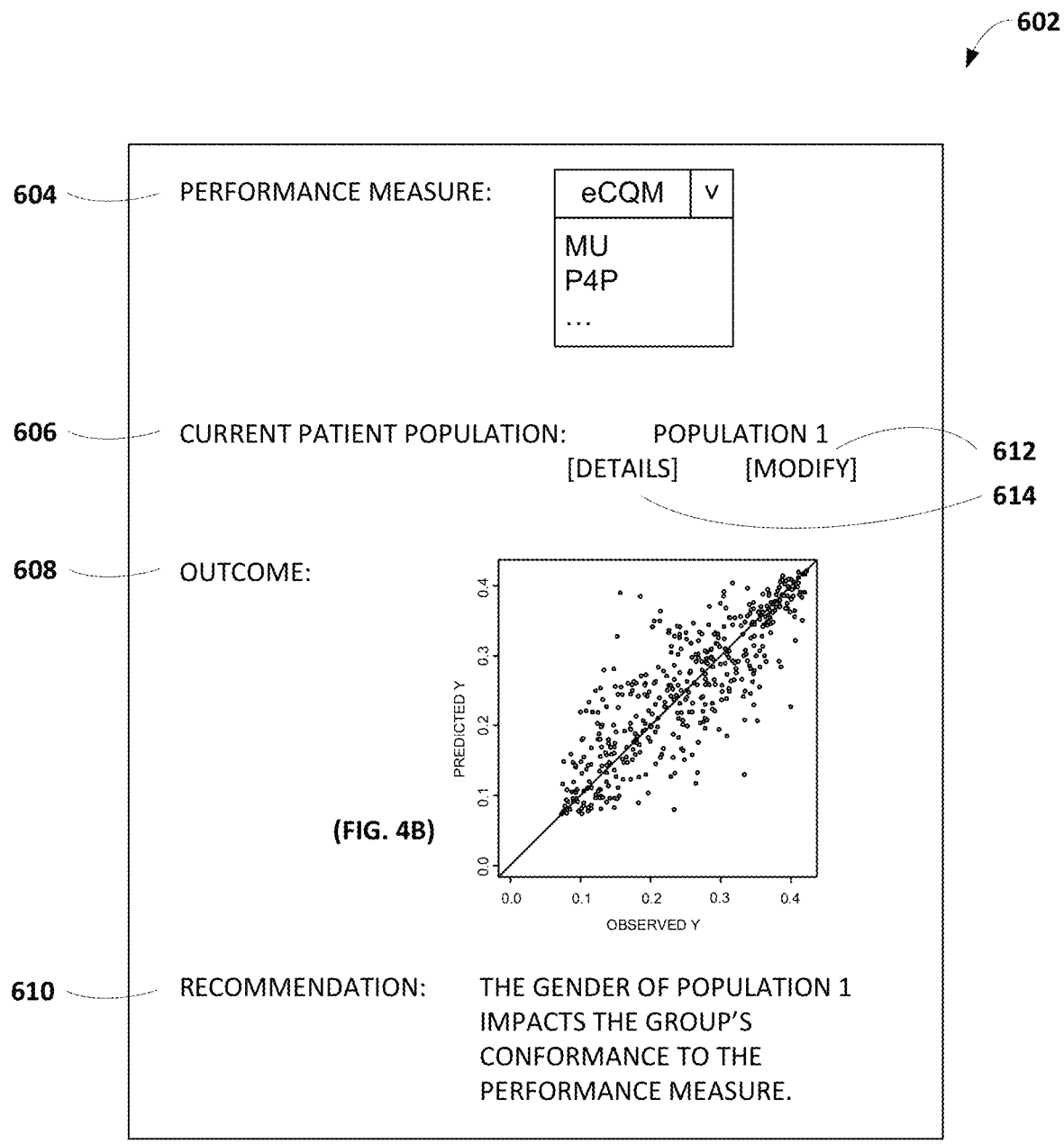
FIG. 6 depicts an exemplary decision support tool user interface according embodiments of the present disclosure.

Referring now to FIG. 6, it depicts an exemplary embodiment that utilizes a graphical user interface 602 to indicate whether specific patient attributes of a patient population results in conformity (or nonconformity) to eCQM, MU, or P4P measures. According to embodiments, the graphical user interface 602, such as the clinician interface 142 of FIG. 1, may present a performance measure indicator 604, a patient data manager 606, and a recommendation as to the conformity of a set of patient attributes 610 ("attribute conformance recommendation"). The graphical user interface 602 may be accessed over the communications network, such as network 175. Alternatively, the graphical user interface 602 may be accessed locally, through an application on a local decision support system. In a further embodiment, to conserve computing resources, a user can remain logged out of the graphical user interface 602 until notified of the nonconformance. As such, the user can subsequently open the graphical user interface 602 and review the determinations made by the clinical decision support system.

In embodiments, the graphical user interface 602 may present the performance measure indicator 604. The performance measure indicator 604 displays the performance measure standard to be applied. The performance measure indicator 604 may present the performance measure standards discussed above, such as eCQM, P4P, and MU. The performance measure indicator 604 may also include the specific clinical quality measure, such as a Meaningful Use Measure NQF-0004 titled "Initiation and Engagement of Alcohol and Other Drug Dependence Treatment." Accordingly, the performance measure indicator 604 presents the performance measure standard that was or will be employed by the decision support system. It is contemplated that, in some aspects, the user may modify the performance standard measure through a drop-down menu or any other suitable means.

In further embodiments, the graphical user interface 602 may present the patient data manager 606. The patient data manager 606, for example, can indicate the current patient data employed by the decision support system. As discussed above, the patient data can be located in one or more databases, such as one or more EHR systems 160, or any one or more other sources of data. In exemplary aspects, the patient data manager 606 can enable the user to modify the patient data for a particular patient or group of patients through a patient data modifier 612. Alternatively or additionally, the patient data manager 606 can present a patient data details option 614, which enables the user to view associated information of the patient data used in the decision support system, such as the attended health-care entity, attended clinician or health-care professional, time period associated the patient data, pool sizes associated with a patient group, and a number of positive counts within the particular pool size. The patient data details option 614 may also enable the presentation of various attributes associated with the patient data, including his or her age category, gender, geographic location, etc.

Figure 4A:
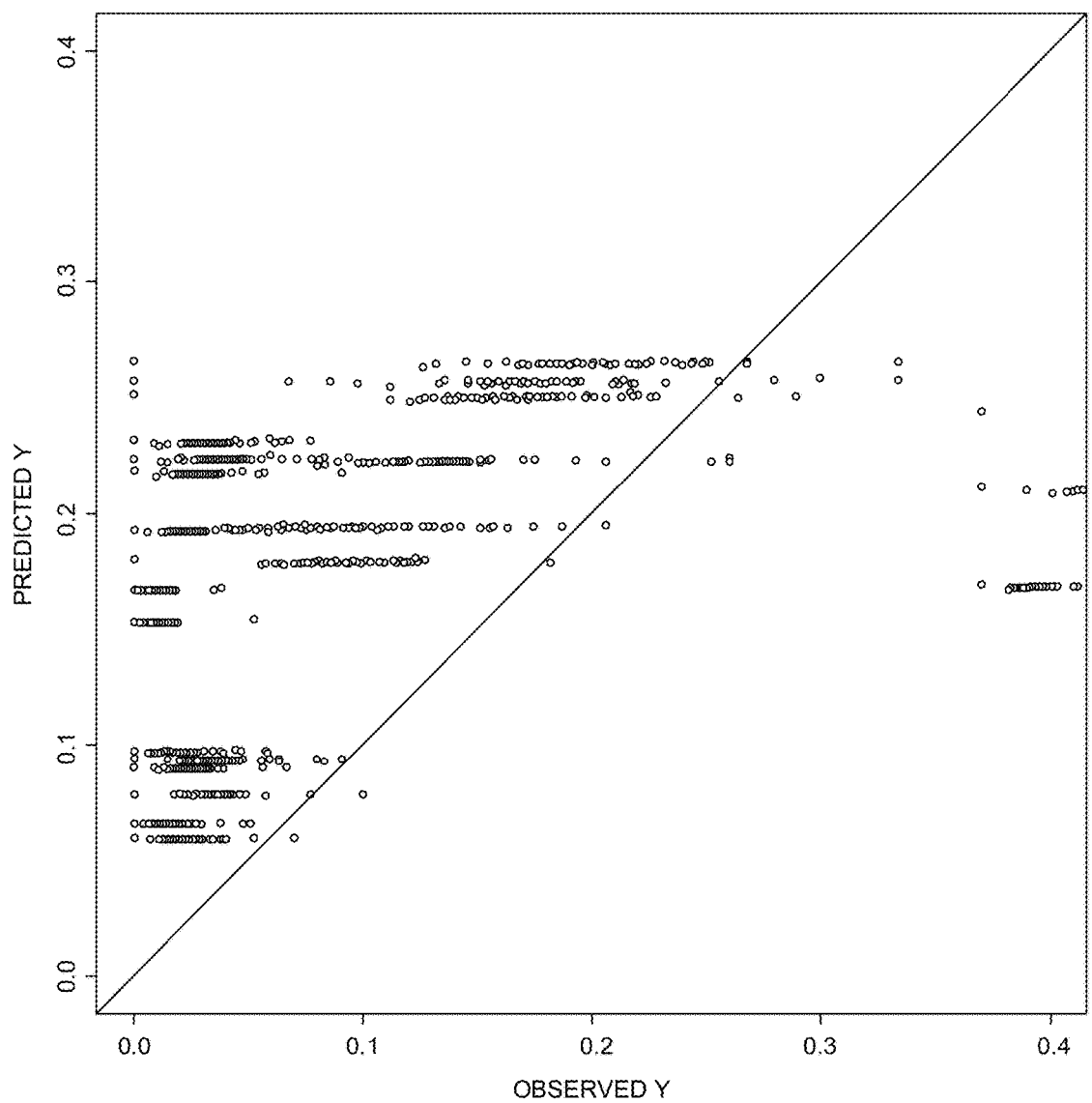
FIGS. 4A and 4B depict aspects of examples showing predicted vs. observed conformity from an embodiment of this technology reduced to practice.
Figure 4B:
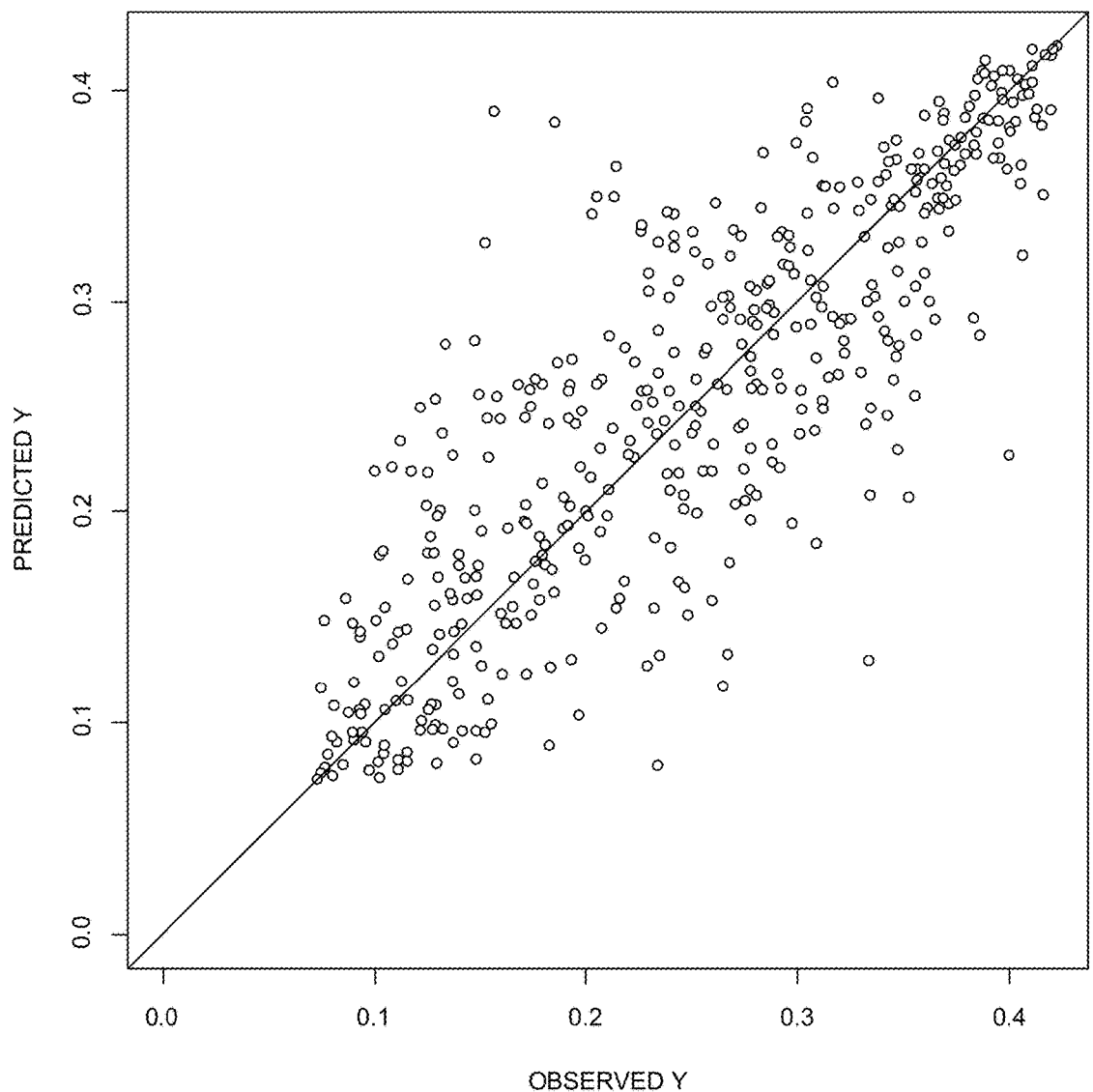

In exemplary embodiments, the graphical user interface 602 may present a model outcome 608 that is specific to the current patient data. For instance, the model outcome may provide the model outcome 608 similar to that which is depicted in FIG. 4B. The model outcome 608 may provide a visual description of the unique determinations made by the decision support system (e.g., those determinations made in method 200).

In one embodiment, the graphical user interface 602 may display the patient attribute conformance recommendation 610 so as to indicate the conformance of various attributes of the patient data to the performance measure standard. In exemplary embodiments, the recommendation may be presented to the user through the use of instructions describing whether certain attributes of the patient population have an effect on that population conforming to performance measure standard. For instance, the patient attribute conformance recommendation 610 may instruct the user that the gender of patients significantly affects the population's conformance to the performance measure of an attending health care professional, as depicted in FIG. 6. It should be appreciated that prior methods or systems were incapable of making these determinations. As such, the current embodiments realize significant technological advantages over established technology since they are able to supply reliable determinations that were previously unattainable, thereby providing enhanced decision support systems.

Example Reduction to Practice

With continuing reference to the drawings, an example embodiment reduced to practice is now described. Reduction to practice was accomplished using a computer running the Linux operating system (operating system 129), the open-source statistical software package R (software services 126), and the R package zoib. DIC metrics for assessing goodness-of-fit were calculated using the R module 'jags.' For the reduction to practice, an observational study of was performed using a consented, secondary-use-rights-granted, de-identified, confidentiality-protected data set. One illustrative example of the practice of the embodiment involves electronic clinical quality measure that is called "Meaningful Use Measure NQF-0004 (Initiation and Engagement of Alcohol and Other Drug [AOD] Dependence Treatment)". NQF-0004 pertains to the percentage of patients 13 years of age and older at the start of the measurement period and having a new episode of alcohol or other drug (AOD) dependency who received treatment via the facility or clinician being evaluated.

Two rates (proportion annualized) are reported: (a) Percentage of patients who initiated treatment within 14 days of the AOD diagnosis; and (b) Percentage of patients who initiated treatment and who had two or more additional treatment sessions for the AOD diagnosis within 30 days of the initiation visit. NQF-0004 is in the domain of Clinical Process/Effectiveness measurement. NQF-0004 involves the retrieval from the EHR utilized by the clinicians those patients 13 years of age and older who were first diagnosed with a new episode of alcohol or drug dependency during a visit within 11 months after the start of the measurement period.

This retrieval forms the denominator of the population to be used under NQF-0004 for the percentages above. This is to be reported as a total score and also by the following age groups: Patients age 13-17; and Patients age >=18. Denominator exclusions are those patients with a previous active diagnosis of alcohol or drug dependence in the 60 days prior to the first episode of alcohol or drug dependence that was documented within the measurement period. (These are to be excluded from the denominator, regardless of whether the patient qualifies for the numerator.) The numerators to be utilized in calculating percentages (a) and (b) are as follows: Numerator (a): Patients in the denominator who initiated treatment within 14 days of the diagnosis; and Numerator (b): Patients in the denominator who initiated treatment, and who had two or more additional services with an AOD diagnosis within 30 days of the initiation visit.

A study was conducted for the reduction-to-practice focused on NQF-0004 part (b). The study involved de-identified, confidentiality-protected records of 56 clinicians who treated 16,829 newly-incident AOD patients (average 301 per clinician per year) from 3 Jan. 2014 through 31 Dec. 2014 in 3 clinic locations. Each of the locations was a regional facility affiliated with a leading AOD treatment network. The case volume in all 3 clinic locations mainly comprised an adult population between the ages of 18 and 64. However, a certain portion of each of the clinicians' practice also involved treating individuals younger than 18 and years of age and older.

Many of the 56 clinicians primarily delivered AOD services via group-therapy sessions while other of the clinicians delivered AOD services predominantly via individual private sessions. The group-therapy-predominant clinicians averaged 522 incident patients during the study interval, while the individual-therapy-predominant clinicians averaged 194 incident patients. If patients are treated in group psychotherapy sessions, the measured conformity percentages may be influenced by the non-individual, group nature of the treatment sessions. Four age categories were defined according to the following ranges: [13-17], [18-39], [40-64], and [65-99] years. The mid-point of each age category was correspondingly set as follows, rounded to the nearest integer: 15, 29, 53, and 83 years.

In this illustrative study of individual and collective performance under NQF-0004b, the analysis embodied by the present invention's system and method revealed that the models where measurement was scoped by clinic location fit very poorly (Example "A", FIG. 4A) in terms of Mean Absolute Prediction Error (MAPE) and other metrics such as DIC. By contrast, if analysis was restricted to one clinic location at a time and the measurement was scoped by clinician (Example "B", FIG. 4B), then the model's predictive performance for NQF 0004b conformity percentage was very good when the predictive variables were gender and age category.

That the majority of variance was not explained by differences in clinic location is not surprising. Nonetheless, it is valuable to be able to determine that location is not significant, so as not to futilely expend money and resources on changing a factor that is not very amenable to remedy and so as not to refrain from further efforts to discover other more amenable factors that contribute to different performance. Socioeconomic or ethnic or other variations that are statistically associated with clinic location would be difficult or impossible to change. Determining that clinic location is not a statistically significant factor is valuable insofar as knowing this is so prevents fruitless expenditure of resources and money.

In this illustrative example, the fact that the majority of variance was explained by differences by clinician and by age and by gender is likewise not surprising. Competent, compassionate clinicians who establish rapport with patients tend to achieve proportionately comparable outcomes in the various clinic locations in which they practice. Less effective, less patient or compassionate clinicians or ones who do not establish rapport with patients tend to experience proportionately lower conformity to outcomes targets in those same locations compared to more competent, compassionate clinicians.

In Example "B" (FIG. 4B), a model that is scoped by clinician and includes gender and age category as explanatory variables reveals strong, actionable statistical relationships with relatively small mean absolute percentage error (MAPE) and other favorable statistical performance metrics. Such a determination serves to justify a variety of practical decisions and actions. First of all, it encourages the identification of clinicians who outperform their colleagues in terms of this quality measure and rewarding them financially or in other ways. Conversely, it supports penalties or compulsory training or other interventions for clinicians who consistently underperform. Educational programs might be developed to enable the salient practices and behaviors of the best performers to be emulated by those who have inferior performance, for example.

Secondly, such a determination serves to support the creation or revision and enhancement of treatment programs oriented to age categories or to genders. Within clinician, the NQF 0004b conformity rate is found to be statistically associated with age category and gender and, therefore, service line or program initiatives that are designed to be consonant with the particular needs and abilities and constraints and perceptions of each gender and/or each age category might be expected to induce improvements in eCQM conformity and, conversely, a health services organization that espouses an age- and gender-agnostic "one size fits all" approach does so at its peril.

In cohorts different from this illustrative reduction-to-practice example, it may happen that models scoped by clinic location might yield good statistical fitting of the data. In such a case, the results may recommend a pay-for-performance regime whereby a clinician's incentive payments are prorated according to her/his different outcome performance in the respective clinic locations.

Collectively, determining fair policies and incentives to motivate high-quality performance and improving outcomes performance on a management planning and population level can have considerable value, for a health services organization and its panel of clinicians and executives or potentially even for a society. Taken together, determinations such as these serve to ameliorate the limitations of prior art cited above under (1) above, namely, aggregating the population into one large category or grouping impairs the ability to analyze the results to determine the factors that are statistically associated with conformity or lack thereof.

Individually, determining fair policies and incentives can promote clinician and patient satisfaction, improvement of care and outcomes, retention of patients who adhere better to prescribed care, and retention of well-performing clinicians in their care delivery roles. This serves to ameliorate the limitations of prior art cited above under (2) above, namely, stability and predictability of the performance results.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

Embodiment 1: A method for evaluating a medical therapy with a computing device, the method comprising: accessing, with the computing device, a data storage system to obtain baseline characteristics for members of a population of patients who each receive a therapy or a bundle comprised of a plurality of therapies; accessing, with the computing device, the data storage system to obtain baseline characteristics and information regarding members of a population of clinician providers who deliver said therapies; accessing, with the computing device, the data storage system to obtain outcome characteristics and information regarding patients treated with the therapies by a set of clinician providers; accessing the data storage system to obtain an indication of a statistical association between at least one of the therapies and at least one aspect of the baseline characteristics and at least one of the outcomes in the subset of the population; modeling, with the computing device, the statistical conformity of the.

Embodiment 2: The method of embodiment 1 further comprising analyzing the patient-provider-outcomes statistical associations by Markov Chain Monte Carlo (MCMC) methods.

Embodiment 3: The method of embodiment 1 further comprising analyzing the patient-provider-outcomes statistical associations by Bayesian Markov Chain Monte Carlo (MCMC) Gibbs Sampler methods.

Embodiment 4: The method of embodiment 1, wherein the at least one outcome is associated with the therapy.

Embodiment 5: The method of embodiment 1, wherein modeling the distribution of the at least one outcome in the population includes estimating the parameters of a beta distribution.

Embodiment 6: The method of embodiment 1, wherein modeling the distribution includes methods for accommodating zero-inflation and, optionally, one-inflation.

Embodiment 7: The method of embodiment 1, wherein modeling the distribution via MCMC involves a "burn-in" series of iterations of sampling to stabilize the sampling process, preferably not less than 1,000 iterations, from which the resulting sampled values are discarded.

Embodiment 8: The method of embodiment 1, wherein modeling the distribution via MCMC involves a series of iterations subsequent to the iterations of claim 7, preferably not less than 4,000 iterations, from which the resulting sampled values are retained for calculating descriptive statistics.

Embodiment 9: The method of embodiment 1 further comprising calculation of the coefficients of the linear or nonlinear equations comprising the model relating the dependent outcome variable to the one or more independent explanatory variables, including provider characteristics, patient characteristics, facility characteristics, or other factors.

Embodiment 10: The method of embodiment 1 further comprising calculation of the parameters of a parametric distribution, such as the beta distribution for the distribution of statistical values of the outcome variable.

Embodiment 11: The method of embodiment 1, wherein the at least one aspect of the baseline characteristics includes one or more of a group consisting of: provider identity; provider specialty; a metric of the skill of the provider associated with the provisioning of the therapy services; provider annualized volume of therapy instances provided; provider venues of service delivery or clinic location.

Embodiment 12: The method of embodiment 1, wherein the at least one post therapy outcome includes one or more of a group consisting of: time to first occurrence of an event; a proportion of patients with a given outcome at a certain point in time; a proportion of patients with a defined plurality of outcome events; a proportion of patients with a defined frequency of outcome events; a patent questionnaire; a clinician patient evaluation; and a medical test result.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A storage media comprising: a non-transitory computer-readable medium having computer-executable instructions embodied thereon that when executed, facilitate performance of a method of predicting, via a decision support system comprising a distributed computing architecture, an estimate of conformity to a medical care performance measure, the method comprising:
   identifying a population of patients who received a particular therapy;
   identifying a set of patients who received the particular therapy, wherein the set of patients is different than the population of patients;
   determining an Electronic Clinical Quality Measures (eCQM) performance measure that identifies a threshold performance based on:
      a first number identifying how many of the set of patients experienced a particular outcome in response to the particular therapy; and
      a second number of patients in the set of patients;
   obtaining a set of patient data for the set of patients, at least a portion of the set of patient data being stored in real-time, wherein the set of patient data includes sets of attribute variables that includes at least one of: an age, gender, treatment location, treating clinician, comorbid condition, prior treatment received, prescribed treatment frequency, prescribed treatment duration, or estimated adherence to a prescribed treatment;
   identifying a set of clinicians that treated the set of patients;
   receiving a set of clinician data corresponding to the set of clinicians;
      distributing and performing parallelized determinations, among a plurality of processors at multiple locations included in the distributed computing architecture, to estimate conformity to the medical care performance measure, wherein the parallelized determinations among the plurality of processors at the multiple locations comprises:
      accessing the set of attribute variables associated with the set of patients;
      analyzing the set of clinician data and the sets of attribute variables using Bayesian Markov Chain Monte Carlo (MCMC) one-inflated beta regression until model convergence is reached;
      from the converged model, extracting a set of one or more regression coefficients and beta distribution parameters;
      from the set of one or more regression coefficients and beta distribution parameters, determining those regression coefficients and beta distribution parameters having a statistical significance thereby forming a subset of statistically significant regression coefficients and beta distribution parameters, wherein each of the subset of statistically significant regression coefficients corresponds to a specific attribute variable of the sets of attribute variable; and
      based on the subset of statistically significant regression coefficients and beta distribution parameters, estimating, without having to actively monitor the set of patient data, a measure of conformity with the eCQM performance measure; and
   automatically displaying, via a display of a user device of the distributed computing architecture, a graphical user interface page that comprises the eCQM performance measure, the measure of conformity with the eCQM performance measure, information characterizing the set of patients, and a recommendation comprising instructions indicating that each of the specific attribute variable has an effect on patients conforming to the eCQM performance measure for the set of patient data, wherein the recommendation further includes policies or methods of other entities that the decision support system has identified as statistically conforming to the eCQM performance measure for the set of patient data.

2. The storage media of claim 1, wherein the Bayesian Markov Chain Monte Carlo (MCMC) one-inflated beta regression is performed using a Gibbs Sampler.

3. The storage media of claim 1, wherein the Bayesian Markov Chain Monte Carlo (MCMC) one-inflated beta regression is performed by first performing a 'burn-in' series of iterations from which sampled distribution values are discarded.

4. The storage media of claim 1, wherein the set of patients is determined based on inclusion-exclusion criteria that comprises a measured time period.

5. The storage media of claim 1 further comprising, enhancing a decision support system by storing the subset of statistically significant regression coefficients and beta distribution parameters in a data store for future retrieval by the decision support system.

6. The storage media of claim 1, wherein statistical significance is determined where $p<0.05$.

7. A storage media comprising: a non-transitory computer-readable medium having computer-executable instructions embodied thereon that when executed, facilitate performance of a method predicting, via a decision support system comprising a distributed computing architecture, an estimate of conformity to a medical care performance measure, the method comprising:
identifying a population of patients who received a particular therapy;
identifying a set of patients who received the particular therapy, wherein the set of patients is different than the population of patients;
determining an Electronic Clinical Quality Measures (eCQM) performance measure that identifies a threshold performance based on:
a first number identifying how many of the set of patients experienced a particular outcome in response to the particular therapy; and
a second number of patients in the set of patients;
identifying a set of clinicians that treated the set of patients;
receiving a set of clinician data corresponding to the set of clinicians;
obtaining a set of patient data for the set of patients, the set of patient data corresponding to a time period of treatment of the population of patients by the set of clinicians, at least a portion of the set of patient data being stored in real-time, wherein the set of patient data includes sets of attribute variables that includes at least one of: an age, gender, treatment location, treating clinician, comorbid condition, prior treatment received, prescribed treatment frequency, prescribed treatment duration, or estimated adherence to a prescribed treatment;
distributing and performing parallelized determinations, among a plurality of processors at multiple locations included in the distributed computing architecture, to estimate conformity to the medical care performance measure, wherein the parallelized determinations among the plurality of processors at the multiple locations comprises:
accessing the sets of attribute variables associated with the set of patients;
analyzing a set of clinician data and the sets of attribute variables using Bayesian Markov Chain Monte Carlo (MCMC) one-inflated beta regression until model convergence is reached;
from the converged model, extracting a set of one or more regression coefficients and beta distribution parameters;
from the set of one or more regression coefficients and beta distribution parameters, determining those regression coefficients and beta distribution parameters having a statistical significance thereby forming a subset of statistically significant regression coefficients and beta distribution parameters, wherein each of the subset of statistically significant regression coefficients corresponds to a specific attribute variable of the sets of attribute variable; and
based on the subset of statistically significant regression coefficients and beta distribution parameters, estimating, without having to actively monitor the set of patient data, a measure of conformity with the eCQM performance measure; and
automatically displaying, via a display of a user device of the distributed computing architecture, a graphical user interface page that comprises the eCQM performance measure, the measure of conformity with the eCQM performance measure, information characterizing the set of patients, and a recommendation comprising instructions indicating that each of the specific attribute variable has an effect on patients conforming to the eCQM performance measure for the set of patient data, wherein the recommendation further includes policies or methods of other entities that the decision support system has identified as statistically conforming to the eCQM performance measure for the set of patient data.

8. The storage media of claim 7, wherein Bayesian Markov Chain Monte Carlo (MCMC) one-inflated beta regression is performed using a Gibbs Sampler.

9. The storage media of claim 7, wherein the Bayesian Markov Chain Monte Carlo (MCMC) one-inflated beta regression is performed by first performing a 'burn-in' series of iterations from which sampled distribution values are discarded.

10. The storage media of claim 9, wherein the 'burn in' series of iterations is not less than 1000.

11. The storage media of claim 7 further comprising, enhancing a decision support system by storing the subset of statistically significant regression coefficients and beta distribution parameters in a data store for future retrieval by the decision support system.

12. The storage media of claim 7, wherein the statistical significance is determined where $p<0.05$.

13. A storage media comprising: a non-transitory computer-readable medium having computer-executable instructions embodied thereon that when executed, facilitate performance of a method for predicting, via a decision support system comprising a distributed computing architecture, an estimate of conformity to a medical care performance measure, the method comprising:
identifying a population of patients who received a particular therapy;
identifying a set of patients who received the particular therapy, wherein the set of patients is different than the population of patients;
determining an Electronic Clinical Quality Measures (eCQM) performance measure that identifies a threshold performance based on:
a first number identifying how many of the set of patients experienced a particular outcome in response to the particular therapy; and
a second number of patients in the set of patients;
identifying a set of clinicians that treated the set of patients;
receiving a set of clinician data corresponding to the set of clinicians;
obtaining a set of patient data for the set of patients, the set of patient data corresponding to a time period of treatment of the population of patients by the set of clinicians, at least a portion of the set of patient data being stored in real-time, wherein the set of patient data includes sets of attribute variables that includes at least one of: an age, gender, treatment location, treating clinician, comorbid condition, prior treatment received, prescribed treatment frequency, prescribed treatment duration, or estimated adherence to a prescribed treatment;

distributing and performing parallelized determinations, among a plurality of processors at multiple locations included in the distributed computing architecture, to estimate conformity to medical care performance measure, wherein the parallelized determinations among the plurality of processors at the multiple locations comprises:

accessing the sets of attribute variables associated with the set of patients;

analyzing a set of clinician data and the sets of one or more attribute variables using Bayesian Markov Chain Monte Carlo (MCMC) zero inflated or one-inflated beta regression until model convergence is reached;

from the converged model, extracting a set of one or more regression coefficients and beta distribution parameters;

from the set of one or more regression coefficients and beta distribution parameters, determining those regression coefficients and beta distribution parameters having a statistical significance thereby forming a subset of statistically significant regression coefficients and beta distribution parameters, wherein each of the subset of statistically significant regression coefficients corresponds to a specific attribute variable of the sets of attribute variable; and based on the subset of statistically significant regression coefficients and beta distribution parameters, determine, without having to actively monitor the set of patient data, estimating a measure of conformity with the eCQM performance measure; and automatically displaying, via a display of a user device of the distributed computing architecture, a graphical interface page that comprises the eCQM performance measure, the measure of conformity with the eCQM performance measure, information characterizing the set of patients, and a recommendation comprising instructions indicating that each of the specific attribute variable has an effect on patients conforming to the eCQM performance measure for the set of patient data, wherein the recommendation further includes policies or methods of other entities that the decision support system has identified as statistically conforming to the eCQM performance measure for the set of patient data.

14. The storage media of claim 13, wherein Bayesian Markov Chain Monte Carlo (MCMC) one-inflated beta regression is performed using a Gibbs Sampler.

15. The storage media of claim 13, wherein the Bayesian Markov Chain Monte Carlo (MCMC) one-inflated beta regression is performed by first performing a 'burn-in' series of iterations from which sampled distribution values are discarded.

16. The storage media of claim 13 further comprising, enhancing a decision support system by storing the subset of statistically significant regression coefficients and beta distribution parameters in a data store for future retrieval by the decision support system.

17. The storage media of claim 13, wherein statistical significance is determined where $p<0.05$.

* * * * *